United States Patent
Wagner

(10) Patent No.: US 9,499,800 B2
(45) Date of Patent: Nov. 22, 2016

(54) METHODS OF MAKING AND USING CHEMICALLY SELF ASSEMBLED-NANORINGS

(71) Applicant: Regents of the University of Minnesota, Minneapolis, MN (US)

(72) Inventor: Carston R. Wagner, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 14/581,538

(22) Filed: Dec. 23, 2014

(65) Prior Publication Data

US 2015/0343082 A1 Dec. 3, 2015

Related U.S. Application Data

(60) Provisional application No. 61/920,921, filed on Dec. 26, 2013.

(51) Int. Cl.
| | | |
|---|---|---|
| *A61K 47/48* | (2006.01) | |
| *A61K 31/519* | (2006.01) | |
| *A61K 39/395* | (2006.01) | |
| *C12N 9/06* | (2006.01) | |
| *C12N 9/96* | (2006.01) | |
| *C07F 9/6561* | (2006.01) | |
| *C07K 16/28* | (2006.01) | |
| *C07K 16/30* | (2006.01) | |

(52) U.S. Cl.
CPC .............. *C12N 9/003* (2013.01); *A61K 31/519* (2013.01); *A61K 47/481* (2013.01); *A61K 47/48046* (2013.01); *A61K 47/48215* (2013.01); *C07F 9/6561* (2013.01); *C07K 16/2803* (2013.01); *C07K 16/30* (2013.01); *C12N 9/96* (2013.01); *C07K 2317/622* (2013.01); *C07K 2317/73* (2013.01); *C12Y 105/01003* (2013.01)

(58) Field of Classification Search
CPC ....... C12N 9/003; C12N 9/96; C07F 9/6561; A61K 47/48246; A61K 31/519
See application file for complete search history.

(56) References Cited

U.S. PATENT DOCUMENTS

| | | | |
|---|---|---|---|
| 5,399,331 A | 3/1995 | Loughrey et al. | |
| 6,774,121 B1 | 8/2004 | Kozak et al. | |
| 8,236,925 B1 | 8/2012 | Wagner et al. | |
| 8,580,921 B2 * | 11/2013 | Wagner | A61K 47/48107 530/300 |
| 2002/0168685 A1 | 11/2002 | Cornish et al. | |
| 2012/0165296 A1 * | 6/2012 | Kratz | A61K 47/48084 514/102 |
| 2015/0017189 A1 | 1/2015 | Wagner et al. | |

FOREIGN PATENT DOCUMENTS

WO 2013109939 A1 7/2013

OTHER PUBLICATIONS

Brentjens, et al., "CD19-targeted T cells rapidly induce molecular remissions in adults with chemotherapy-refractory acute lymphoblastic leukemia", Sci Transl Med 5 (177), 177ra38, 19 pages (2013).
Carlson, et al., "Chemically controlled self-assembly of protein nanorings", J Am Chem Soc 128 (23), 7630-7638 (2006).
Chandra, et al., "Programmable cell adhesion encoded by DNA hybridization", Angew Chem Int Ed Engl 45 (6), 896-901 (2006).
Cheng, et al., "Nanoparticulate cellular patches for cell-mediated tumoritropic delivery", ACS Nano 4 (2), 625-631 (2010).
Chou, et al., "Enzyme nanorings", ACS Nano 2 (12), 2519-2525 (2008).
Curran, et al., "Chimeric antigen receptors for T cell immunotherapy: current understanding and future directions", J Gene Med 14 (6), 405-415 (2012).
De Kruif, et al., "Recombinant lipid-tagged antibody fragments as functional cell-surface receptors", Nat Med 6 (2), 223-227 (2000).
Dutta, et al., "Engineering cell surfaces via liposome fusion", Bioconjug Chem 22 (12) 2423-2433 (2011).
Dutta, et al., "Synthetic chemoselective rewiring of cell surfaces: generation of three-dimensional tissue structures", J Am Chem Soc 133 (22), 8704-8713 (2011).
Fegan, et al., "Chemically controlled protein assembly: techniques and applications", Chem. Rev 110 (6), 3315-3336 (2010).
Fegan, et al., "Chemically self-assembled antibody nanostructures as potential drug carriers", Mol. Pharm. 9 (11), 3218-3227 (2012).
Gabrielse, et al., "Engineering T-cell Surfaces for Tumor Cell Killing with Chemically Self-Assembled Antibody Nanorings (CSANS)", Keystone Meeting on Antibodies as Drugs, Vancouver, BC., Poster and Abstract (Jan. 27-Feb. 1, 2013).
Gangar, et al., "Programmable self-assembly of antibody-oligonucleotide conjugates as small molecule and protein carriers", J. Am. Chem. Soc., 134 (6), 2895-2897 (2012).
Gangar, et al., "Targeted delivery of antisense oligonucleotides by chemically self-assembled nanostructures", Mol Pharm 10(9), 3514-3518 (2013).
Gulati, et al., "Lipophilic drug derivatives in liposomes", International Journal of Pharmaceutics vol. 165 (2), 129-168 (1998).
Ko, et al., "Targeting mesenchymal stem cells to activated endothelial cells", Biomaterials 30 (22), 3702-3710 (2009).
Li et al., "Chemically self-assembled antibody nanorings (CSANs): design and characterization of an anti-CD3 IgM biomimetic", J. Am. Chem. Soc. 132 (48), 17247-17257 (2010).
Li, et al., "Self-assembly of antibodies by chemical induction", Angew Chem Int Ed Engl 47 (52), 10179-10182 (2008).
Pignatello, et al., "Lipophilic conjugates of methotrexate with glucosyl-lipoamino acids: calorimetric study of the interaction with a biomembrane model", Thermochimica Acta, vol. 426 (1-2), 163-171 (2005).
Pignatello, et al., "Structural effects of lipophilic methotrexate conjugates on model phospholipid biomembranes", Thermochimica Acta, vol. 380 (2), 255-264 (2001).

(Continued)

*Primary Examiner* — Yong Chu
(74) *Attorney, Agent, or Firm* — Viksnins Harris & Padys PLLP

(57) ABSTRACT

Provided herein are compounds, conjugates and methods for making lipid-chemically self-assembled nanorings (Lipid-CSANs) and using them to treat diseases and modify cell surfaces.

19 Claims, 14 Drawing Sheets

(56) References Cited

OTHER PUBLICATIONS

Porter, et al., "Chimeric antigen receptor-modified T cells in chronic lymphoid leukemia", N Engl J Med 365 (8), 725-733 (2011).

Rabuka, et al., "Site-specific chemical protein conjugation using genetically encoded aldehyde tags", Nat Protoc 7 (6), 1052-1067 (2012).

Stephan, et al., "Enhancing cell therapies from the outside in: Cell surface engineering using synthetic nanomaterials", Nano Today 6, 309-325 (2011).

Swiston, et al., "Surface functionalization of living cells with multilayer patches", Nano Lett 8 (12), 4446-4453 (2008).

Wagner, et al., "Reversible re-programing of cell-cell interactions", Angew Chem Int Ed Engl 53 (20), 5112-5116 (2014).

Williams, et al., "Synthesis of methotrexate-dimyristoylphosphatidylethanolamine analogs and characterization of methotrexate release in vitro", International Journal of Pharmaceutics, vol. 85, 189-197 (1992).

Wilson, et al., "Layer-by-layer assembly of a conformal nanothin PEG coating for intraportal islet transplantation", Nano Lett 8 (7), 1940-1948 (2008).

* cited by examiner

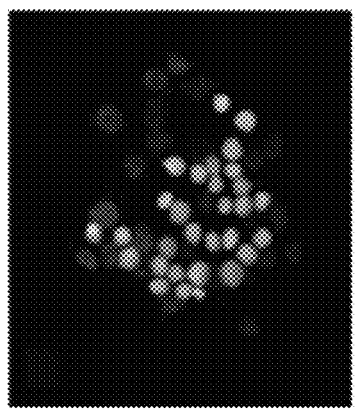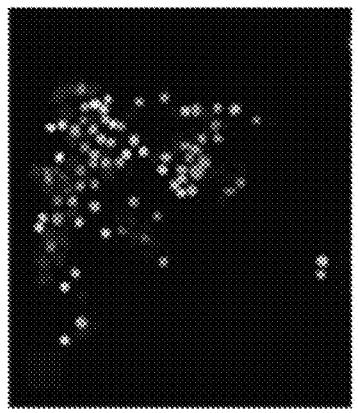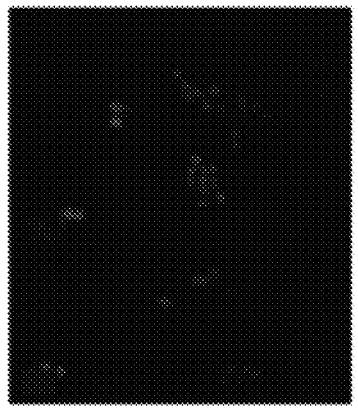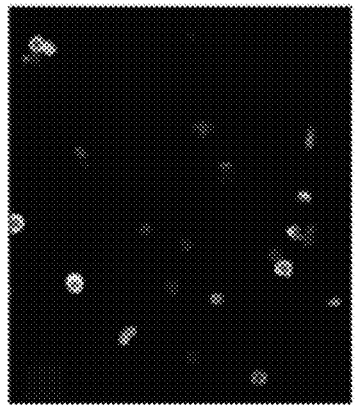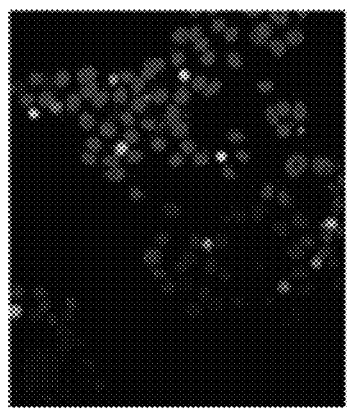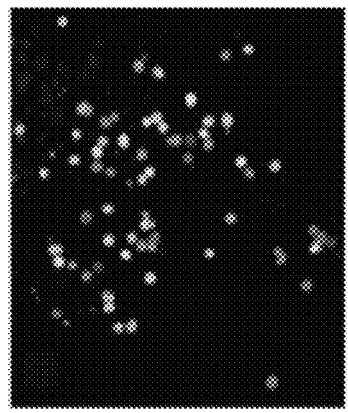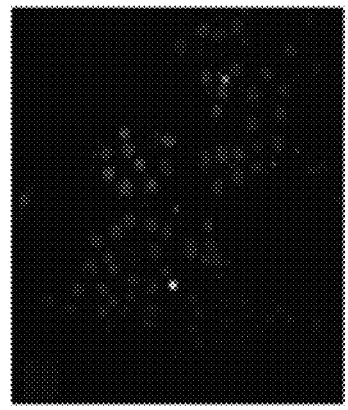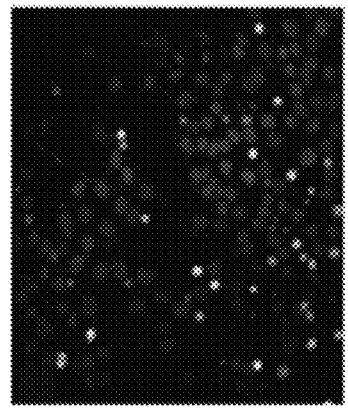

METHODS OF MAKING AND USING CHEMICALLY SELF ASSEMBLED-NANORINGS

RELATED APPLICATION

This patent application claims the benefit of priority of U.S. Application Ser. No. 61/920,921 filed Dec. 26, 2013. The content of this provisional application is hereby incorporated herein in its entirety.

STATEMENT OF GOVERNMENT SUPPORT

This invention was made with government support under CA125360 and CA120116 awarded by the National Cancer Institute.

BACKGROUND

The ability to coordinate and control cell-cell interactions is a pre-requisite for the evolution and development of multicellular life forms. Tissues and organs, such as the central nervous system and immune system, for example, are composed of multiple cellular types. The functioning of these systems is highly dependent on the expression of cell membrane ligands and receptors that direct the interaction between cells. The development of approaches for the controlled display of ligands and receptors on cell surfaces would greatly facilitate the ability to manipulate the interactions of cells with other cells and tissues. In addition, these methodologies may also have potential also be used to track the behavior of cells in vivo by labeling cells with either optical, radiological or MRI detectable probes.

A number of approaches have been devised for the re-engineering of cell surfaces (Stephan, M. T. I., D. J. Enhancing Cell Therapies from the Outside In: Cell Surface Engineering using Synthetic Nanomaterials. Nano Today 6, 309-325, 2011). Certain methods have taken advantage of the promiscuity of glycan biosynthesis to randomly terminate cell surface glycoproteins with azido-neuramimic acid, followed by conjugation by click chemistry to oligonucleotides (Chandra, R. A., et al. Programmable cell adhesion encoded by DNA hybridization. Angewandte Chemie-International Edition 45, 896-901, doi:10.1002/anie.200502421, 2006), thus enabling control over cell-cell interactions by differential conjugation to complementary oligonucleotides (David Rabuka, et al. Site-specific Chemical Protein Conjugation using Genetically Encoded Aldehyde Tags. Nature Protocol 7, 1052-1066, 2012). Chemical cross-linking methods have also been developed that rely on the random biotinylation of cell surface macromolecules, followed by tethering to a ligand through avidin binding (Cheng, H. et al. Nanoparticulate Cellular Patches for Cell-Mediated Tumoritropic Delivery. ACS Nano 4, 625-631, doi:10.1021/nn901319y, 2010). The lack of specificity of these approaches may lead to unforeseen disruptions in either intracellular and extracellular glycoprotein biosynthesis or cell membrane function. In addition, while covalent modifications are highly stable, depending on the turnover of the membrane protein or oligosaccharide, they are not reversible.

Non-covalent cell surface modification approaches have received far less attention. Membrane intercalating proteins or peptides have been conjugated to a phospholipid or fatty acids or linked recombinantly to glycosylphosphatidylinositol (GPI) (Ko, I. K., et al. Targeting mesenchymal stem cells to activated endothelial cells. Biomaterials 30, 3702-3710, doi:10.1016/j.biomaterials.2009.03.038, 2009). Chemically reactive fatty acids have been incorporated into liposomes and when allowed to fuse to cell membranes provide chemical conjugation sites to cellular membranes (Dutta, D., et al. Engineering Cell Surfaces via Liposome Fusion. Bioconjugate Chemistry 22, 2423-2433, doi:10.1021/bc200236m, 2011; Dutta, D., et al. Synthetic Chemoselective Rewiring of Cell Surfaces: Generation of Three-Dimensional Tissue Structures. Journal of the American Chemical Society 133, 8704-8713, doi:10.1021/ja2022569, 2011). Although, reactive fatty acids have been shown to distribute to the membranes of other cellular organelles, the ability to control cell adhesion to surfaces, including other cells, has been demonstrated (Dutta, D., et al. Bioconjugate Chemistry 22, 2423-2433, doi:10.1021/bc200236m, 2011; Dutta, D., et al. Journal of the American Chemical Society 133, 8704-8713, doi:10.1021/ja2022569, 2011). Unfortunately, although membrane protein function may not be directly affected, the association half-life of proteins conjugated to fatty acids or phospholipids is relatively short, ranging from one to two hours (Ko, I. K., et al. Targeting mesenchymal stem cells to activated endothelial cells. Biomaterials 30, 3702-3710, doi:10.1016/j.biomaterials. 2009.03.038, 2009; de Kruif, J., et al. Recombinant lipid-tagged antibody fragments as functional cell-surface receptors. Nat. Med. 6, 223-227, doi: 10.1038/72339, 2000). Non-cytotoxic polymers have been used to coat cells, while methods have been developed for adhering polyelectrolyte multilayer (PEM) patches to cells using photolithography (Wilson, J. T., et al. Layer-by-layer assembly of a conformal nanothin PEG coating for intraportal islet transplantation. Nano Letters 8, 1940-1948, doi:10.1021/nl080694q, 2008; Swiston, A. J. et al. Surface Functionalization of Living Cells with Multilayer Patches. Nano Letters 8, 4446-4453, doi:10.1021/nl802404h, 2008). While the stability of the association of either polymer or electrolytes to cells is impressive, the modifications are irreversible and, particularly for photolithography, the number of cells that can be modified is limiting. Other surface modification methods are those that rely on molecular biological techniques to genetically engineer cells to express receptors or ligands. For example, T-cells of Adult Lymphocytic Leukemia (ALL) patients have been engineered to express an anti-CD 19 single-chain antibody fused to CD3ε, referred to as chimeric antigen receptors (CARs) (Porter, D. L., et al. Chimeric Antigen Receptor-Modified T cells in chronic Lymphoid Leukemia. The New England Journal of Medicine 365, 725-734, 2011). The engineered CARS T-cells have demonstrated the ability to suppress B-lymphocytic tumor growth clinically (Brentjens, R. J. et al. CD19-Targeted T Cells Rapidly Induce Molecular Remissions in Adults with Chemotherapy-Refractory Acute Lymphoblastic Leukemia. Science Translational Medicine 5, doi: 10.1126/scitranslmed.3005930, 2013; Porter, D. L. et al Chimeric Antigen Receptor T Cells Directed Against CD19 Induce Durable Responses and Transient Cytokine Release Syndrome in Relapsed, Refractory CLL and ALL. Blood 120, 2012). Nevertheless, the relatively low transfection efficiency of these methods and the unknown clinical outcome of long lived genetically modified cells are challenges that remain to be addressed (Curran, K., et al. Chimeric Antigen Receptors for T cell Immunotherapy: Current Understanding and future directions. The Journal of Gene Medicine 14, 405-415, 2012). Consequently, a non-genetic approach that would allow the rapid, stable and reversible modification of membranes with one or more ligands would provide a complementary synthetic biological tool for the re-programming of cell surfaces.

A method for the engineering and preparation of chemically self-assembled nanorings (CSANs) has been developed (Carlson, J. C. T. et al. Chemically controlled self-assembly of protein nanorings. J. Amer. Chem. Soc. 128, 7630-7638, 2006). CSANs are prepared by taking advantage of the power of high affinity chemically-induced dimerization (Fegan, A., et al. Chemically controlled protein assembly: Techniques and applications. Chem. Rev. 110, 3315-3336, 2010). When mixed with a covalently linked dimer of the dihydrofolate reductase (DHFR) inhibitor methotrexate (bisMTX), DHFR forms highly robust protein dimers with an affinity of approximately $10^{-11}$ M (Carlson, J. J. Amer. Chem. Soc. 128, 7630-7638, 2006). When one DHFR is recombinantly fused through an encoded linker peptide to another DHFR (yielding DHFR-DHFR or DHFR$^2$), spontaneous and rapid self-assembly into CSANs was observed, whose diameter is dependent on the length and composition of the linker peptide (13-amino acid linker=dimer, 1-amino acid linker=octamer) (Li, Q., et al. Self-Assembly of Antibodies by Chemical Induction. Angewandte Chemie-International Edition 47, 10179-10182, doi:10.1002/anie.200803507, 2008); Li, Q. et al. Chemically Self-Assembled Antibody Nanorings (CSANs): Design and Characterization of an Anti-CD3 IgM Biomimetic. J. Amer. Chem. Soc. 132, 17247-17257, doi:10.1021/ja107153a, 2010). The rings exhibit high stability with $T_m$s ranging from 63-66° C. Single molecule experiments have also confirmed that even at picomolar concentrations, nearly 70% of the nanorings remain intact. Since the CSANs exhibit the properties of a stable scaffold, CSANs recombinantly fused to single-chain antibodies (scFvs) and peptides that target cell surface receptors were prepared (Li, Q., et al. Angewandte Chemie-International Edition 47, 10179-10182, doi:10.1002/anie.200803507, 2008; Li, Q. et al. Biomimetic. J. Amer. Chem. Soc. 132, 17247-17257, doi: 10.1021/ja107153a, 2010; Gangar, A. et al. Targeted delivery of antisense oigonucleotides by chemically self-assembled nanostructures (CSANs). Mol. Pharmaceutics (ASAP), 2013). The resulting monovalent, bivalent or octavalent targeted-CSANs were found to selectively bind targeted cellular receptors. For example, octavalent anti-CD3 CSANs were shown to bind CD3+ lymphocytic cells with an affinity of 0.9 nM (Li, Q., et al. Angewandte Chemie-International Edition 47, 10179-10182, doi:10.1002/anie.200803507, 2008; Li, Q. et al. Biomimetic. J. Amer. Chem. Soc. 132, 17247-17257, doi:10.1021/ja107153a, 2010), while CSANs displaying the cyclic-RGD peptide were shown to target $\alpha_v\beta_3$ on breast cancer cells (Gangar, A. et al. Mol. Pharmaceutics (ASAP), 2013). Recently, the utility of CSANs has been expanded through the design and preparation of new bisMTX chemical dimerizers that contain a third arm with a reactive group capable of being conjugated to fluorophores, drugs and oligonucleotides (Gangar, A. et al. Mol. Pharmaceutics (ASAP), 2013; Fegan, A., et al. Chemically self-assembled antibody nanostructures as potential drug carriers. Mol. Pharmaceutics 9, 3218-3227, 2012; Gangar, A., et al. Programmable Self-Assembly of Antibody-Oligonucleotide Conjugates as Small Molecule and Protein Carriers. J. Amer. Chem. Soc. 134, 2895-2897, doi:10.1021/ja210894g, 2012). In addition, it has been demonstrated that CSANs can undergo rapid disassembly, both extra- and intracellularly, in the presence of clinically relevant doses of the non-toxic FDA approved bacterial DHFR inhibitor, trimethoprim; thus affording pharmacological and therefore temporal control of their interactions with cells and tissues(Li, Q., et al. Angewandte Chemie-International Edition 47, 10179-10182, doi:10.1002/anie.200803507, 2008; Li, Q. et al. Biomimetic. J. Amer. Chem. Soc. 132, 17247-17257, doi:10.1021/ja107153a, 2010; Fegan, A., Kumarapperuma, S. C. & Wagner, C. R. Chemically self-assembled antibody nanostructures as potential drug carriers. Mol. Pharmaceutics 9, 3218-3227, 2012). Accordingly, there is a need to develop agents including CSANs for the modification or re-engineering of cell surfaces for such uses as interrogation of cellular interactions in vitro and/or in vivo or the design of cell or tissue-based therapies such as the treatment of diseases (e.g., cancer).

SUMMARY OF CERTAIN EMBODIMENTS OF THE INVENTION

Certain embodiments provide a compound of formula I:

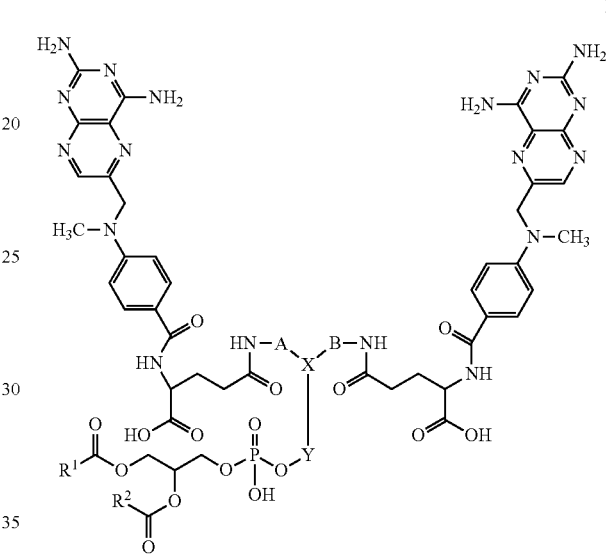

wherein:

A is a divalent, branched or unbranched, saturated or unsaturated, hydrocarbon chain, having from 2 to 25 carbon atoms, wherein one or more of the carbon atoms is optionally replaced by (—O—), and wherein the chain is optionally substituted on carbon with one or more substituents selected from ($C_1$-$C_6$)alkoxy, ($C_3$-$C_6$)cycloalkyl, ($C_1$-$C_6$) alkanoyl, ($C_1$-$C_6$)alkanoyloxy, ($C_1$-$C_6$)alkoxycarbonyl, ($C_1$-$C_6$)alkylthio, azido, cyano, nitro, halo, hydroxy, oxo (=O), carboxy, aryl, aryloxy, heteroaryl, and heteroaryloxy;

B is a divalent, branched or unbranched, saturated or unsaturated, hydrocarbon chain, having from 2 to 25 carbon atoms, wherein one or more of the carbon atoms is optionally replaced by (—O—), and wherein the chain is optionally substituted on carbon with one or more substituents selected from ($C_1$-$C_6$)alkoxy, ($C_3$-$C_6$)cycloalkyl, ($C_1$-$C_6$) alkanoyl, ($C_1$-$C_6$)alkanoyloxy, ($C_1$-$C_6$)alkoxycarbonyl, ($C_1$-$C_6$)alkylthio, azido, cyano, nitro, halo, hydroxy, oxo (=O), carboxy, aryl, aryloxy, heteroaryl, and heteroaryloxy;

X is N or

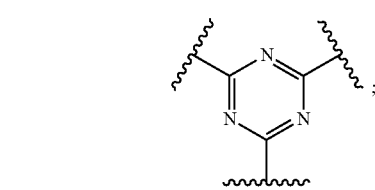 [SMILES: *c1nc(*)nc(*)n1]

Y is a suitable linking group;

$R^1$ is a branched or unbranched, saturated or unsaturated, hydrocarbon chain, having from 3 to 30 carbon atoms; and $R^2$ is a branched or unbranched, saturated or unsaturated, hydrocarbon chain, having from 3 to 30 carbon atoms;

or a salt thereof.

Certain embodiments provide a compound of formula Ia:

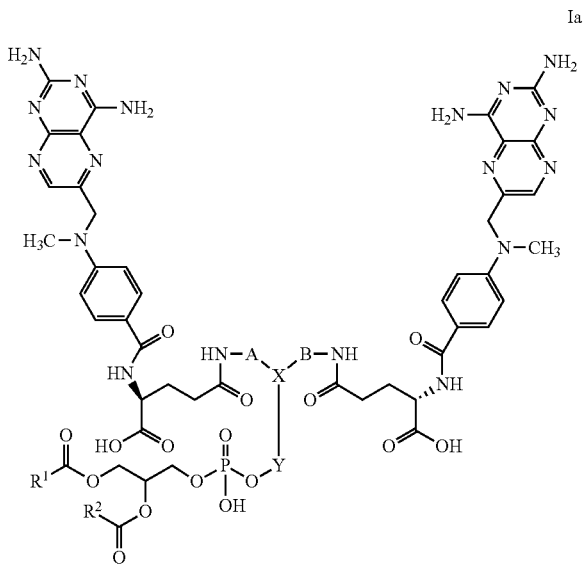

Ia wherein:

A is a divalent, branched or unbranched, saturated or unsaturated, hydrocarbon chain, having from 2 to 25 carbon atoms (e.g., 3-10 carbon atoms in length, 5-10 carbon atoms in length), wherein one or more (e.g. 1, 2, 3, 4, 5 or more) of the carbon atoms is optionally replaced by (—O—), and wherein the chain is optionally substituted on carbon with one or more (e.g., 1, 2, 3, 4, 5 or more) substituents selected from ($C_1$-$C_6$)alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, cyano, nitro, halo, hydroxy, oxo (=O), carboxy, aryl, aryloxy, heteroaryl, and heteroaryloxy;

B is a divalent, branched or unbranched, saturated or unsaturated, hydrocarbon chain, having from 2 to 25 carbon atoms (e.g., 3-10 carbon atoms in length, 5-10 carbon atoms in length), wherein one or more (e.g. 1, 2, 3, 4, 5 or more) of the carbon atoms is optionally replaced by (—O—), and wherein the chain is optionally substituted on carbon with one or more (e.g. 1, 2, 3, 4, 5 or more) substituents selected from ($C_1$-$C_6$)alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, cyano, nitro, halo, hydroxy, oxo (=O), carboxy, aryl, aryloxy, heteroaryl, and heteroaryloxy;

X is N or

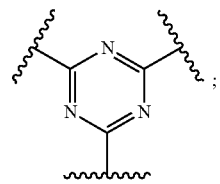 [SMILES: *c1nc(*)nc(*)n1]

;

Y is a suitable linking group;

$R^1$ is a branched or unbranched, saturated or unsaturated, hydrocarbon chain, having from 3 to 30 carbon atoms; and $R^2$ is a branched or unbranched, saturated or unsaturated, hydrocarbon chain, having from 3 to 30 carbon atoms;

or a salt thereof.

One embodiment provides a conjugate comprising a compound of formula I or a pharmaceutically acceptable salt thereof as described herein, wherein the conjugate further comprises a first dihydrofolate reductase (DHFR) molecule linked to second DHFR molecule via a linker.

One embodiment provides a composition comprising a compound of formula I or a pharmaceutically acceptable salt thereof as described herein or a conjugate of formula I or a pharmaceutically acceptable salt thereof as described herein and a pharmaceutically acceptable carrier.

One embodiment provides a method for treating cancer in a patient in need of such treatment, comprising administering to the patient a therapeutically effective amount of a compound of formula I or a pharmaceutically acceptable salt thereof as described herein or a conjugate of formula I or a pharmaceutically acceptable salt as described herein.

One embodiment provides a compound of formula I or a pharmaceutically acceptable salt thereof as described herein or a conjugate of formula I or a pharmaceutically acceptable salt thereof as described herein for use in medical treatment or diagnosis.

One embodiment provides the use of a compound of formula I or a pharmaceutically acceptable salt thereof as described herein or a conjugate of formula I or a pharmaceutically acceptable salt thereof as described herein to prepare a medicament useful for treating cancer in an mammal.

One embodiment provides a compound of formula I or a pharmaceutically acceptable salt thereof as described herein or a conjugate of formula I or a pharmaceutically acceptable salt thereof as described herein for use in therapy.

One embodiment provides a compound of formula I or a pharmaceutically acceptable salt thereof as described herein or a conjugate of formula I or a pharmaceutically acceptable salt thereof as described herein for use in treating cancer.

One embodiment provides a method to modify the surface of a cell comprising contacting the cell in vitro or in vivo with a compound of formula I or a pharmaceutically acceptable salt thereof as described herein or a conjugate of formula I or a pharmaceutically acceptable salt thereof as described herein.

One embodiment provides processes and intermediates disclosed herein that are useful for preparing a compound of formula I or a salt thereof or a conjugate of formula I or a salt thereof.

BRIEF DESCRIPTION OF THE FIGURES

FIGS. 1 A-C shows the assembly and disassembly of Lipid-CSANs.

FIGS. 3A1-A4 and 3B1-B4 shows the association and dissociation of Lipid-CSANs: (FIGS. 3A1-A4) Confocal Microscopy images showing the spontaneous insertion of the lipid into the T-cell membrane and subsequent cell-cell interactions. HPB-MLT cells treated for 1 hour with Bodipy labeled bivalent Lipid-CSANs allowing the spontaneous insertion of the Lipid CSANs into the cell surface to be observed, with the DAPI stained nucleus (FIG. 3A1). Control MCF-7 cells incubated with untreated HPB-MLT (T-leukemia cells, DAPI stained nucleus) (FIG. 3A2). The ability of anti-EpCAM T-cells to cause a cell-cell interaction was observed by incubating HPB-MLT cells (CFSE stained) pretreated with bivalent (FIG. 3A3) or octavalent (FIG. 3A4) anti-EpCAM lipid CSANs, respectively, and MCF-7 (EpCAM positive cell line, DAPI stained nucleus) cells for 1 hour. Following the incubation, cells were washed and fixed, and the presence of cell-cell interactions observed using confocal microscopy. (FIGS. 3B1-B4) Confocal microscopy images showing dissociation of cell-cell interactions after treatment with trimethoprim (TMP). HPB-MLT cells (CFSE stained) treated with anti-EpCAM lipid CSANs and incubated with MCF-7 cells (DAPI stained nucleus), followed by washing with media, demonstrating that the cell-cell interactions remain intact (FIG. 3B1). HPB-MLT cells (CFSE stained) treated with bivalent anti-EpCAM Lipid-CSANs and incubated with MCF-7 cells (DAPI stained nucleus), followed by a treatment with excess TMP, demonstrating successful disassembly of the cell-cell interactions (FIG. 3B2). HPB-MLT cells (CFSE stained) treated with octavalent anti-EpCAM Lipid-CSANs incubated with MCF-7 cells (DAPI stained nucleus), followed by washing, demonstrating that the cell-cell interactions remain intact (FIG. 3B3). HPB-MLT cells (CFSE stained) treated with octavalent anti-EpCAM Lipid-CSANs incubated with MCF-7 cells (DAPI stained nucleus), followed by a treatment with excess TMP, demonstrating successful disassembly of the cell-cell interactions (FIG. 3B4). (See Example for details and Table S1 for cell binding statistics).

(FIG. 4A) Lysis of MCF-7 breast cancer cells over a four-hour incubation time with activated T-cells at varying effector to target (E:T) ratios. (Squares) Enhanced cell lysis can be observed in the presence of redirected octavalent antiEpCAM Lipid-CSANs treated activated T-cells. (diamonds)*=P<0.0025 (FIG. 4B) Anti-EpCAM Lipid-CSANs concentration-dependent cell lysis. Activated PBMCs were treated with varying concentrations of anti-EpCAM Lipid-CSANs, and were then incubated with MCF-7 cells at an E:T ratio of 10:1. *=P<0.003, **=P≤0.05 (FIG. 4C) Cell-specific lysis upon incubation with anti-EpCAM Lipid-CSANs modified T-cells visualized over 20 hours (0, 5, 15 and 20 hour time points shown) through time-lapse video microscopy. Cells were cultured at a ratio of two MCF-7 cells to two U87 cells to one PBMC. The left column depicts a coculture of MCF-7 breast cancer cells (EpCAM+) and U87 glioblastoma cells (EpCAM-) that has been treated with activated T-cells. In the right-hand column, octavalent anti-EpCAM Lipid-CSANs redirected towards the EpCAM+ MCF-7 cells show an enhanced, cell-specific lysis of MCF-7 cells over EpCAM-U87 cells. White arrows point towards healthy U87 cells, while the white dotted circle encompasses a group of targeted MCF-7 cells. (See Example for experimental details).

(FIG. 7A) Cells following the initial 30-minute incubation and first media removal. (FIG. 7B) Cells after second media removal at one hour. (FIG. 7C) Cells after third media removal at ninety minutes. (FIG. 7D) Cells after fourth media removal at two hours. (FIG. 7E) Cells after fifth media removal at two and a half hours. (FIG. 7F) Cells after final media removal at three hours. (FIG. 7G) HPB-MLT cells treated with 1 µM 13DDBodipy lipid-CSANs for twenty-four hours. (FIG. 7H) HPB-MLT cells treated with 1 µM 13DDBodipy lipid-CSANs for forty-eight hours. (FIG. 7I) HPB-MLT cells treated with 1 µM 13DDBodipy lipid-CSANs for seventy-two hours.

DETAILED DESCRIPTION

Figure 1A:
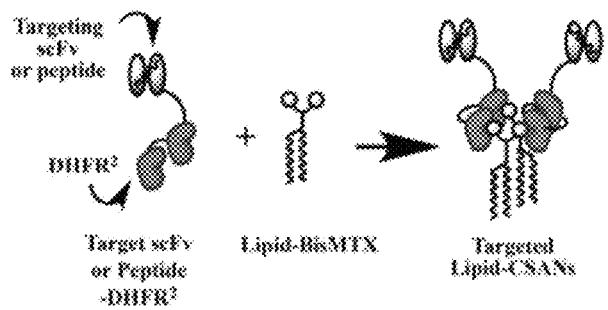
(FIG. 1A) Schematic representation showing the self-assembling formation of the lipid CSANs from a recombinant fusion protein of DHFR-DHFR ($DHFR^2$) and a targeting scFv or peptide.
Figure 1B:
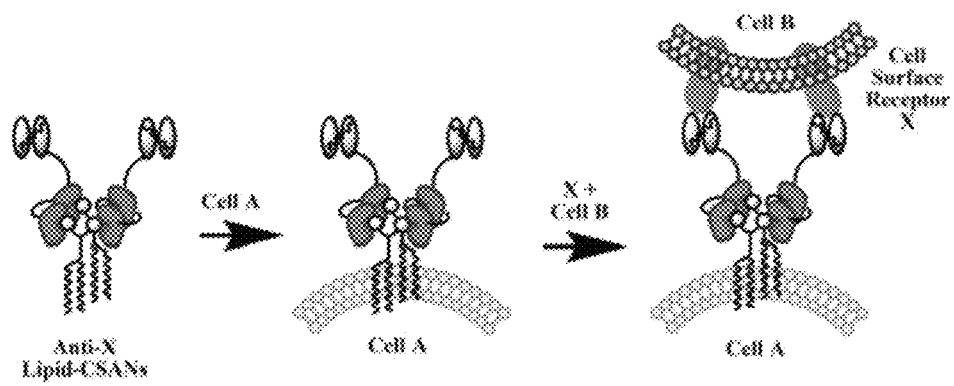
(FIG. 1B) Schematic representation showing the spontaneous insertion of the lipid CSANs into the lipid bilayer of a cell membrane, followed by a second incubation with the target cells that over-express receptor (X) resulting in directed cell-cell interactions.
Figure 1C:
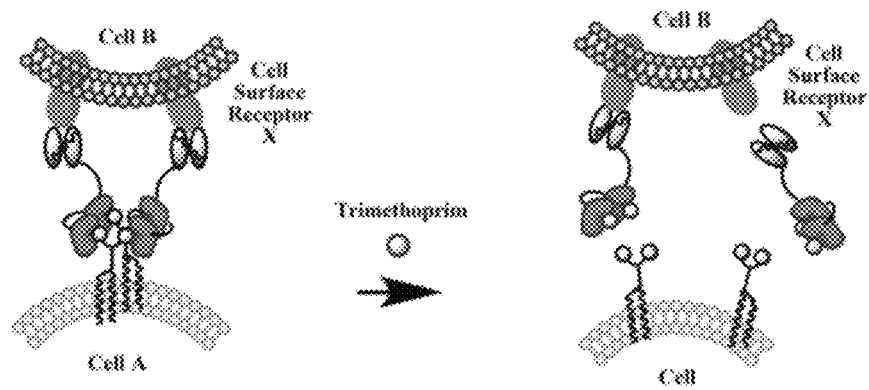
(FIG. 1C) Following directed cell-cell interactions, the lipid CSANs can be induced to undergo rapid disassembly in the presence of an excess of trimethoprim, a non-toxic FDA approved antibiotic; thus allowing temporal control over the cell surface modification and engineered cell-cell interactions.

A new cell surface engineering strategy using lipid-chemically self-assembled nanorings (Lipid-CSANs) that can be used for the stable and reversible modification of any cell surface with a molecular reporter or targeting ligand has been developed. Site specific labeled bivalent and octavalent Lipid-CSANs have been prepared and which can quickly (<15 min) and stably (>72 h) intercalate into cell membranes. In addition, Lipid-CSANs fused to a single-chain antibody (scFv) targeting the carcinoma and cancer stem cell marker EpCAM have been prepared and it has been demonstrated that cells functionalized with the anti-EpCAM-Lipid-CSANs selectively bind EpCAM positive cancer cells. In the presence of a non-toxic FDA approved drug, the nanorings were quickly disassembled and the cell-cell interactions reversed. Similar to T-cells genetically engineered to express chimeric antigen receptors (CARS), when activated peripheral blood mononuclear cells (PBMCs) were functionalized with the anti-EpCAM-Lipid-CSANs, they were shown to selectively kill antigen positive cancer cells. Thus, Lipid-CSANs have the potential to be a rapid, stable and general method for the reversible engineering of cell surfaces and cell-cell interactions.

The following definitions are used, unless otherwise described: halo is fluoro, chloro, bromo, or iodo. Alkyl, alkoxy, alkenyl, alkynyl, etc. denote both straight and branched groups; but reference to an individual radical such as propyl embraces only the straight chain radical, a branched chain isomer such as isopropyl being specifically referred to. An unsaturated hydrocarbon chain is a hydrocarbon chain that has one or more unsaturated groups (i.e., alkene or alkyne groups). Aryl denotes a phenyl radical or an ortho-fused bicyclic carbocyclic radical having about nine to ten ring atoms in which at least one ring is aromatic. Heteroaryl encompasses a radical of a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_4)$alkyl, phenyl or benzyl, as well as a radical of an ortho-fused bicyclic heterocycle of about eight to ten ring atoms comprising one to four heteroatoms each selected from the group consisting of non-peroxide oxygen, sulfur, and N(X).

The term "heterocyclyl" or "heterocycle" as used herein refers to a single saturated or partially unsaturated ring that has at least one atom other than carbon in the ring, wherein the atom is selected from the group consisting of oxygen, nitrogen and sulfur. Thus, the term includes single saturated or partially unsaturated rings (e.g., 3, 4, 5, 6 or 7-membered rings) from about 1 to 6 carbon atoms and from about 1 to 3 heteroatoms selected from the group consisting of oxygen, nitrogen and sulfur in the ring. The ring may be substituted with one or more (e.g., 1, 2 or 3) oxo groups and the sulfur and nitrogen atoms may also be present in their oxidized forms. It is to be understood that the point of attachment of a heterocycle can be at any suitable atom of the heterocycle including a carbon atom and a heteroatom (e.g., a nitrogen). Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl and pyrrolidine-2,5-dionyl.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

Specific values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$alkanoyl can be acetyl, propanoyl or butanoyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_2-C_6)$alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the mixture of compounds is at least 51% the absolute stereoisomer depicted. In another embodiment, the mixture of compounds is at least 60% the absolute stereoisomer depicted. In another embodiment, the mixture of compounds is at least 80% the absolute stereoisomer depicted. In another embodiment, the mixture of compounds is at least 90% the absolute stereoisomer depicted. In another embodiment, the mixture of compounds is at least 95% the absolute stereoisomer depicted. In another embodiment, the mixture of compounds is at least 99% the absolute stereoisomer depicted.

The linking group Y is any group that connects the phospholipid of formula I with the rest of the molecule of formula I in a manner to retain the useful properties of the phospholipid CSANs. The linking group typically has a molecular weight of from about 200 daltons to about 25,000 daltons and is a divalent, branched or unbranched, saturated or unsaturated, hydrocarbon chain, having from 20 to 250 carbon atoms, wherein one or more of the chain carbon atoms is optionally replaced by O, S, $NR^a$, (C=O) or a 5 or 6-membered heterocycle, wherein each $R^a$ is independently H or $(C_1-C_6)$alkyl, and wherein the chain is optionally substituted on carbon with one or more substituents selected from $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo (=O), carboxy, aryl, aryloxy, heteroaryl and heteroaryloxy. In one embodiment the O, S and NR$^a$ groups of the chain are not adjacent to any other O, S and NR$^a$ groups of the chain.

Specific values listed below are values for compounds of formula I and all sub-formulas of I (e.g., compounds of formula Ia, Ib). It is to be understood that one or more values may be combined with one or more additional values.

A specific group of compounds of formula I are compounds of formula Ib:

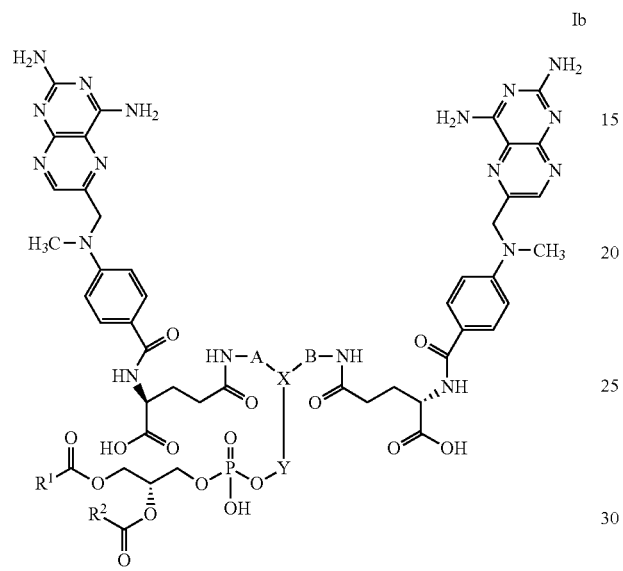

Ib or a salt thereof.

A specific value for A is a divalent, branched or unbranched, saturated or unsaturated, hydrocarbon chain, having from 3 to 10 carbon atoms, wherein one or more carbon atoms is optionally replaced with an oxygen (—O—) atom in the chain, wherein the chain is optionally substituted on carbon with one or more substituents selected from ($C_1$-$C_6$)alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, cyano, nitro, halo, hydroxy, oxo (=O), carboxy, aryl, aryloxy, heteroaryl, and heteroaryloxy.

A specific value for A is a divalent, branched or unbranched, saturated or unsaturated, hydrocarbon chain, having from 3 to 10 carbon atoms, wherein one or more carbon atoms is optionally replaced with an oxygen (—O—) atom in the chain.

A specific value for A is a divalent, branched or unbranched, saturated or unsaturated, hydrocarbon chain, having from 3 to 10 carbon atoms.

A specific value for A is a divalent, branched or unbranched, saturated or unsaturated, hydrocarbon chain, having from 3 to 7 carbon atoms.

A specific value for A is an unbranched ($C_3$-$C_{10}$)alkylene chain.

A specific value for A is —$(CH_2)_5$—.

A specific value for B is a divalent, branched or unbranched, saturated or unsaturated, hydrocarbon chain, having from 3 to 10 carbon atoms, wherein one or more carbon atoms is optionally replaced with an oxygen (—O—) atom in the chain, wherein the chain is optionally substituted on carbon with one or more substituents selected from ($C_1$-$C_6$)alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, cyano, nitro, halo, hydroxy, oxo (=O), carboxy, aryl, aryloxy, heteroaryl, and heteroaryloxy.

A specific value for B is a divalent, branched or unbranched, saturated or unsaturated, hydrocarbon chain, having from 3 to 10 carbon atoms, wherein one or more carbon atoms is optionally replaced with an oxygen (—O—) atom in the chain.

A specific value for B is a divalent, branched or unbranched, saturated or unsaturated, hydrocarbon chain, having from 3 to 10 carbon atoms.

A specific value for B is a divalent, branched or unbranched, saturated or unsaturated, hydrocarbon chain, having from 3 to 7 carbon atoms.

A specific value for B is an unbranched ($C_3$-$C_{10}$)alkylene chain.

A specific value for B is —$(CH_2)_5$—.

A specific value for X is N.

A specific value for X is

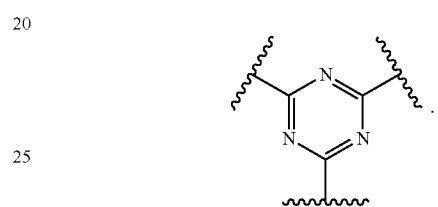

A specific value for $R^1$ is a branched or unbranched, saturated or unsaturated, hydrocarbon chain, having from 10 to 25 carbon atoms.

A specific value for $R^1$ is a branched or unbranched, saturated, hydrocarbon chain, having from 10 to 25 carbon atoms.

A specific value for $R^1$ is an unbranched, saturated, hydrocarbon chain, having from 15 to 20 carbon atoms.

A specific value for $R^1$ is —$(CH_2)_{16}CH_3$.

A specific value for $R^2$ is a branched or unbranched, saturated or unsaturated, hydrocarbon chain, having from 10 to 25 carbon atoms.

A specific value for $R^2$ is a branched or unbranched, saturated, hydrocarbon chain, having from 10 to 25 carbon atoms.

A specific value for $R^2$ is an unbranched, saturated, hydrocarbon chain, having from 15 to 20 carbon atoms.

A specific value for $R^2$ is —$(CH_2)_{16}CH_3$.

A specific group of compounds of formula I are compounds wherein Y has a molecular weight of from about 200 daltons to about 25,000 daltons.

A specific group of compounds of formula I are compounds wherein Y has a molecular weight of from about 200 daltons to about 20,000 daltons.

A specific group of compounds of formula I are compounds wherein Y has a molecular weight of from about 200 daltons to about 15,000 daltons.

A specific group of compounds of formula I are compounds wherein Y has a molecular weight of from about 200 daltons to about 10,000 daltons.

A specific group of compounds of formula I are compounds wherein Y has a molecular weight of from about 200 daltons to about 5,000 daltons.

A specific group of compounds of formula I are compounds wherein Y has a molecular weight of from about 200 daltons to about 3,000 daltons.

A specific group of compounds of formula I are compounds wherein Y has a length of about 30 angstroms to about 500 angstroms.

A specific group of compounds of formula I are compounds wherein Y has a length of about 75 angstroms to about 500 angstroms.

A specific group of compounds of formula I are compounds wherein Y has a length of about 100 angstroms to about 500 angstroms.

A specific group of compounds of formula I are compounds wherein Y has a length of about 150 angstroms to about 500 angstroms.

A specific value for Y is a divalent, branched or unbranched, saturated or unsaturated, hydrocarbon chain, having from 20 to 250 carbon atoms, wherein one or more of the chain carbon atoms is optionally replaced by O, S, $NR^a$, (C=O) or a 5 or 6-membered heterocycle, wherein each $R^a$ is independently H or $(C_1$-$C_6)$alkyl, and wherein the chain is optionally substituted on carbon with one or more substituents selected from $(C_1$-$C_6)$alkoxy, $(C_3$-$C_6)$cycloalkyl, $(C_1$-$C_6)$alkanoyl, $(C_1$-$C_6)$alkanoyloxy, $(C_1$-$C_6)$alkoxycarbonyl, $(C_1$-$C_6)$alkylthio, azido, cyano, nitro, halo, hydroxy, oxo (=O), carboxy, aryl, aryloxy, heteroaryl and heteroaryloxy.

A specific value for Y is a divalent, branched or unbranched, saturated or unsaturated, hydrocarbon chain, having from 20 to 250 carbon atoms, wherein one or more of the chain carbon atoms is optionally replaced by O, S, $NR^a$, (C=O) or a 5 or 6-membered heterocycle and wherein each $R^a$ is independently H or $(C_1$-$C_6)$alkyl.

A specific value for Y is a divalent, branched or unbranched, saturated or unsaturated, hydrocarbon chain, having from 50 to 250 carbon atoms, wherein one or more of the chain carbon atoms is optionally replaced by O, S, $NR^a$, (C=O) or a 5 or 6-membered heterocycle and wherein each $R^a$ is independently H or $(C_1$-$C_6)$alkyl.

A specific value for Y is a divalent, branched or unbranched, saturated or unsaturated, hydrocarbon chain, having from 100 to 250 carbon atoms, wherein one or more of the chain carbon atoms is optionally replaced by O, S, $NR^a$, (C=O) or a 5 or 6-membered heterocycle and wherein each $R^a$ is independently H or $(C_1$-$C_6)$alkyl.

A specific value for Y is a divalent, branched or unbranched, saturated or unsaturated, hydrocarbon chain, having from 100 to 200 carbon atoms, wherein one or more of the chain carbon atoms is optionally replaced by O, S, $NR^a$, (C=O) or a 5 or 6-membered heterocycle and wherein each $R^a$ is independently H or $(C_1$-$C_6)$alkyl.

A specific value for Y is a divalent, branched or unbranched, saturated or unsaturated, hydrocarbon chain, having from 20 to 250 carbon atoms, wherein one or more of the chain carbon atoms is optionally replaced by O, S, $NR^a$ or (C=O) wherein each $R^a$ is independently H or $(C_1$-$C_6)$alkyl and wherein 1, 2 or 3 of the chain carbon atoms is optionally replaced by a 5 or 6-membered heterocycle, and wherein the chain is optionally substituted on carbon with one or more substituents selected from $(C_1$-$C_6)$alkoxy, $(C_3$-$C_6)$cycloalkyl, $(C_1$-$C_6)$alkanoyl, $(C_1$-$C_6)$alkanoyloxy, $(C_1$-$C_6)$alkoxycarbonyl, $(C_1$-$C_6)$alkylthio, azido, cyano, nitro, halo, hydroxy, oxo (=O), carboxy, aryl, aryloxy, heteroaryl and heteroaryloxy.

A specific value for Y is a divalent, branched or unbranched, saturated or unsaturated, hydrocarbon chain, having from 20 to 250 carbon atoms, wherein one or more of the chain carbon atoms is optionally replaced by O, S, $NR^a$ or (C=O) wherein each $R^a$ is independently H or $(C_1$-$C_6)$alkyl and wherein 1, 2 or 3 of the chain carbon atoms is optionally replaced by a 5 or 6-membered heterocycle.

A specific value for Y is a divalent, branched or unbranched, saturated or unsaturated, hydrocarbon chain, having from 50 to 250 carbon atoms, wherein one or more of the chain carbon atoms is optionally replaced by O, S, $NR^a$ or (C=O) wherein each $R^a$ is independently H or $(C_1$-$C_6)$alkyl and wherein 1, 2 or 3 of the chain carbon atoms is optionally replaced by a 5 or 6-membered heterocycle.

A specific value for Y is a divalent, branched or unbranched, saturated or unsaturated, hydrocarbon chain, having from 100 to 250 carbon atoms, wherein one or more of the chain carbon atoms is optionally replaced by O, S, $NR^a$ or (C=O) wherein each $R^a$ is independently H or $(C_1$-$C_6)$alkyl and wherein 1, 2 or 3 of the chain carbon atoms is optionally replaced by a 5 or 6-membered heterocycle.

A specific value for Y is a divalent, branched or unbranched, saturated or unsaturated, hydrocarbon chain, having from 100 to 200 carbon atoms, wherein one or more of the chain carbon atoms is optionally replaced by O, S, $NR^a$ or (C=O) wherein each $R^a$ is independently H or $(C_1$-$C_6)$alkyl and wherein 1, 2 or 3 of the chain carbon atoms is optionally replaced by a 5 or 6-membered heterocycle.

A specific value for Y is a divalent, branched or unbranched, saturated or unsaturated, hydrocarbon chain, having from 20 to 250 carbon atoms, wherein one or more of the chain carbon atoms is optionally replaced by O, S, $NR^a$ or (C=O) wherein each $R^a$ is independently H or $(C_1$-$C_6)$alkyl and wherein 1, 2 or 3 of the chain carbon atoms is optionally replaced by a 5-membered heterocycle, and wherein the chain is optionally substituted on carbon with one or more substituents selected from $(C_1$-$C_6)$alkoxy, $(C_3$-$C_6)$cycloalkyl, $(C_1$-$C_6)$alkanoyl, $(C_1$-$C_6)$alkanoyloxy, $(C_1$-$C_6)$alkoxycarbonyl, $(C_1$-$C_6)$alkylthio, azido, cyano, nitro, halo, hydroxy, oxo (=O), carboxy, aryl, aryloxy, heteroaryl and heteroaryloxy.

A specific value for Y is a divalent, branched or unbranched, saturated or unsaturated, hydrocarbon chain, having from 20 to 250 carbon atoms, wherein one or more of the chain carbon atoms is optionally replaced by O, S, $NR^a$ or (C=O) wherein each $R^a$ is independently H or $(C_1$-$C_6)$alkyl and wherein 1, 2 or 3 of the chain carbon atoms is optionally replaced by a 5-membered heterocycle.

A specific value for Y is a divalent, branched or unbranched, saturated or unsaturated, hydrocarbon chain, having from 50 to 250 carbon atoms, wherein one or more of the chain carbon atoms is optionally replaced by O, S, $NR^a$ or (C=O) wherein each $R^a$ is independently H or $(C_1$-$C_6)$alkyl, alkyl and wherein 1, 2 or 3 of the chain carbon atoms is optionally replaced by a 5-membered heterocycle.

A specific value for Y is a divalent, branched or unbranched, saturated or unsaturated, hydrocarbon chain, having from 100 to 250 carbon atoms, wherein one or more of the chain carbon atoms is optionally replaced by O, S, $NR^a$ or (C=O) wherein each $R^a$ is independently H or $(C_1$-$C_6)$alkyl and wherein 1, 2 or 3 of the chain carbon atoms is optionally replaced by a 5-membered heterocycle.

A specific value for Y is a divalent, branched or unbranched, saturated or unsaturated, hydrocarbon chain, having from 100 to 200 carbon atoms, wherein one or more of the chain carbon atoms is optionally replaced by O, S, $NR^a$ or (C=O) wherein each $R^a$ is independently H or $(C_1$-$C_6)$alkyl and wherein 1, 2 or 3 of the chain carbon atoms is optionally replaced by a 5-membered heterocycle.

A specific value for the 5-membered heterocycle as provided for in any of the above values is

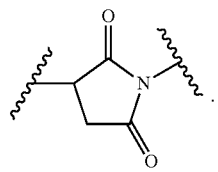 [SMILES: *C1CC(=O)N(*)C1=O]

A specific value for Y is a radical of formula A'-B'-C'-D'-E'-F'-G'-H'-I'; wherein:
A' is —(CH$_2$CH$_2$O)$_{1-5}$—;
B' is —(C$_1$-C$_6$)alkyl-NR$^{a'}$(C=O)— or —(C$_1$-C$_6$)alkyl-O(C=O)—;
C' is —(CH$_2$CH$_2$O)$_{2-8}$—;
D' is —(C$_1$-C$_6$)alkyl-X—
E' is absent or is a 5 or 6-membered heterocycle;
F' is —(C$_1$-C$_6$)alkyl-NR$^{a'}$(C=O)— or —(C$_1$-C$_6$)alkyl-O(C=O)—;
G' is —(CH$_2$CH$_2$O)$_{20-70}$—;
H' is —C(=O)NR$^{a'}$—(C$_1$-C$_6$)alkyl- or —C(=O)O—(C$_1$-C$_6$)alkyl-,
X is O, S or NR$^{a'}$; and
R$^{a'}$ is H or (C$_1$-C$_6$)alkyl.
A specific compound of formula I is:

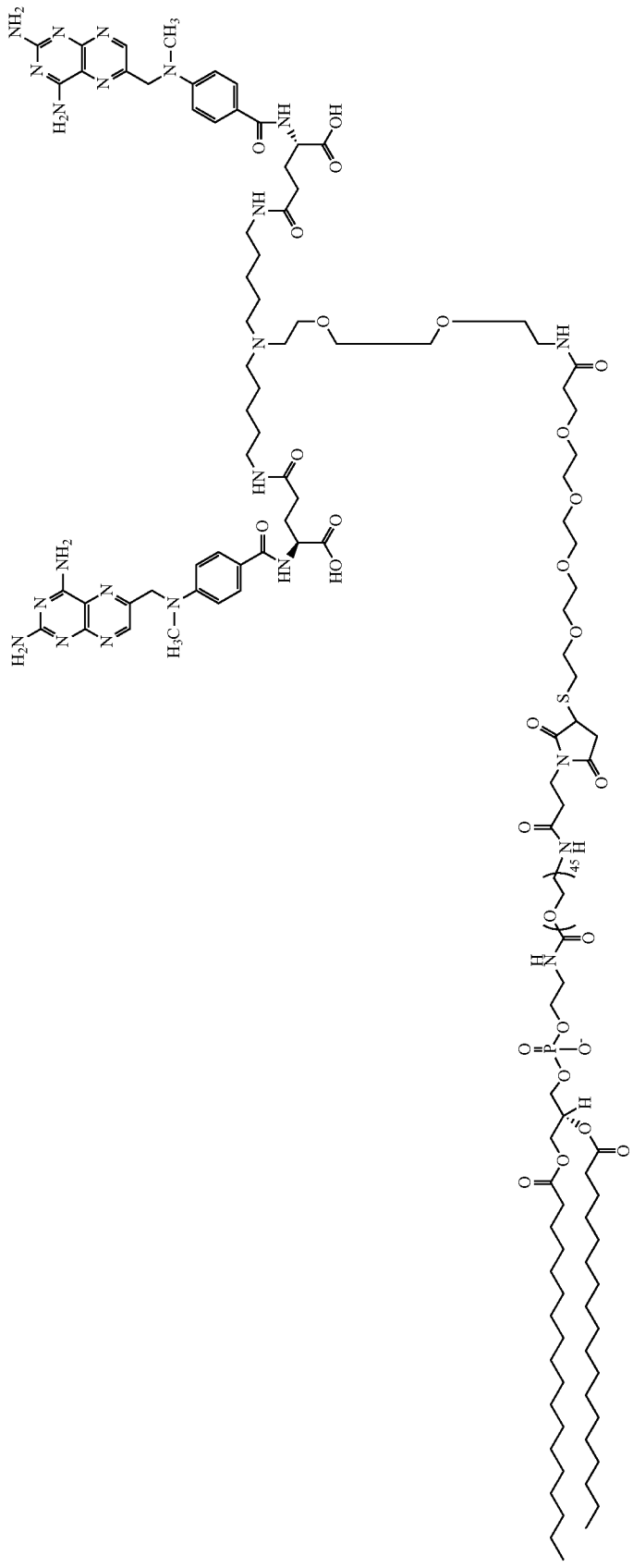

or a salt thereof.

One embodiment provides a conjugate comprising a compound of formula I or a pharmaceutically acceptable salt as described herein, wherein the conjugate further comprises a first dihydrofolate reductase (DHFR) molecule linked to second DHFR molecule via a linker.

A used herein the linker which links a first dihydrofolate reductase (DHFR) molecule to a second DHFR molecule is any suitable group that functions to connect the two DHFR molecules together while retaining the useful properties of the connected DHFR molecules. In one embodiment the linker comprises about 2 atoms to about 10,000 atoms. In one embodiment the linker comprises about 2 atoms to about 5000 atoms. In one embodiment the linker comprises about 2 atoms to about 2000 atoms. In one embodiment the linker comprises about 2 atoms to about 1000 atoms. In one embodiment the linker comprises about 2 atoms to about 500 atoms. In one embodiment the linker comprises about 2 atoms to about 200 atoms. In one embodiment the linker comprises about 2 atoms to about 100 atoms. In one embodiment the linker comprises about 10 atoms to about 10,000 atoms. In one embodiment the linker comprises about 10 atoms to about 5000 atoms. In one embodiment the linker comprises about 10 atoms to about 2000 atoms. In one embodiment the linker comprises about 10 atoms to about 1000 atoms. In one embodiment the linker comprises about 10 atoms to about 500 atoms. In one embodiment the linker comprises about 10 atoms to about 200 atoms. In one embodiment the linker comprises about 10 atoms to about 100 atoms. In one embodiment the linker comprises about 20 atoms to about 10,000 atoms. In one embodiment the linker comprises about 20 atoms to about 5000 atoms. In one embodiment the linker comprises about 20 atoms to about 2000 atoms. In one embodiment the linker comprises about 20 atoms to about 1000 atoms. In one embodiment the linker comprises about 20 atoms to about 500 atoms. In one embodiment the linker comprises about 20 atoms to about 200 atoms. In one embodiment the linker comprises about 20 atoms to about 100 atoms. It is to be understood that the atoms in the linking group can be arranged in any manner including for example, but not limited to branched, unbranched and cyclic atom arrangements. In one embodiment the atoms of the linker are arranged in a branched or unbranched manner. The atoms of linker can be selected from any suitable atoms. In one embodiment the atoms are selected from carbon, hydrogen, oxygen, nitrogen and sulfur atoms. One particular linker is a linker which comprises an amino acid or a polypeptide. In one embodiment the linker comprises about 1 amino acid to about 200 amino acids. In one embodiment the linker comprises about 1 amino acid to about 150 amino acids. In one embodiment the linker comprises about 1 amino acid to about 100 amino acids. In one embodiment the linker comprises about 1 amino acid to about 50 amino acids. In one embodiment the linker comprises about 1 amino acid to about 20 amino acids. In one embodiment the linker comprises about 1 amino acid to about 15 amino acids. In one embodiment the linker comprises about 1 amino acid to about 10 amino acids. In one embodiment the polypeptide linker comprises about 2 amino acids to about 200 amino acids. In one embodiment the polypeptide linker comprises about 2 amino acids to about 150 amino acids. In one embodiment the polypeptide linker comprises about 2 amino acids to about 100 amino acids. In one embodiment the polypeptide linker comprises about 2 amino acids to about 50 amino acids. In one embodiment the polypeptide linker comprises about 2 amino acids to about 20 amino acids. In one embodiment the polypeptide linker comprises about 2 amino acids to about 15 amino acids. In one embodiment the polypeptide linker comprises about 2 amino acids to about 10 amino acids. In one embodiment the polypeptide linker comprises about 3 amino acids to about 50 amino acids. In one embodiment the polypeptide linker comprises about 3 amino acids to about 20 amino acids. In one embodiment the polypeptide linker comprises about 3 amino acids to about 15 amino acids. In one embodiment the polypeptide linker comprises about 3 amino acids to about 10 amino acids. In one embodiment the polypeptide linker comprises about 5 amino acids to about 50 amino acids. In one embodiment the polypeptide linker comprises about 5 amino acids to about 20 amino acids. In one embodiment the polypeptide linker comprises about 5 amino acids to about 20 amino acids. In one embodiment the polypeptide linker comprises about 10 amino acids to about 20 amino acids.

In one embodiment the conjugate further comprises a targeting molecule.

In one embodiment the targeting molecule selectively recognizes an antigen on a cancer cell.

In one embodiment the targeting molecule is a single-chain variable fragment (scFv).

In one embodiment the targeting molecule is anti-Ep-CAM.

One embodiment provides a conjugate comprising a compound of formula I or a pharmaceutically acceptable salt as described herein, wherein the conjugate further comprises (a) a first dihydrofolate reductase (DHFR) molecule linked to second DHFR molecule via a linker and (b) a cell capable of inducing apoptosis.

The term "conjugate" as used herein includes compounds of formula I that interact or bind to other compounds. Thus, the individual components of the conjugate may interact via non-valent bonds.

In one embodiment the cell capable of inducing apoptosis is an activated peripheral blood mononuclear cell.

In one embodiment the cell capable of inducing apoptosis is a T cell.

Certain general categories and examples of antigens can be found at www.ncbi.nlm.nih.gov/booksNBK12961/ and in the Table below. One embodiment provides a targeting molecule that selectively recognizes an antigen as described in www.ncbi.nlm.nih.gov/booksNBK12961/ or in the Table below.

| General Categories and Examples of Tumor Antigens | | |
|---|---|---|
| Category | Example Antigen | Cancer Histology |
| Oncofetal | CEA | Colorectal carcinoma |
| | Immature laminin receptor | RCC |
| | TAG-72 | Prostate carcinoma |
| Oncoviral | HPV E6, E7 | Cervical carcinoma |
| Overexpressed/accumulated | BING-4 | Melanoma |
| | Calcium-activated | Lung carcinoma |

-continued

General Categories and Examples of Tumor Antigens

| Category | Example Antigen | Cancer Histology |
|---|---|---|
| | chloride channel 2 | |
| | Cyclin-$B_1$ | Multi |
| | 9D7 | RCC |
| | Ep-CAM | Breast carcinoma |
| | EphA3 | Multi |
| | Her2/neu | Multi |
| | Telomerase | Multi |
| | Mesothelin | Ductal pancreatic carcinoma |
| | SAP-1 | Colorectal carcinoma |
| | Survivin | Multi |
| Cancer-Testis | BAGE family | Multi |
| | CAGE family | Multi |
| | GAGE family | Multi |
| | MAGE family | Multi |
| | SAGE family | Multi |
| | XAGE family | Multi |
| CT9, CT10 | | Multi |
| | NY-ESO-1/LAGE-1 | Multi |
| | PRAME | Multi |
| | SSX-2 | Melanoma, Multi |
| Lineage Restricted | Melan-A/MART-1 | Melanoma |
| | Gp100/pmel17 | Melanoma |
| | Tyrosinase | Melanoma |
| | TRP-1/-2 | Melanoma |
| | P.polypeptide | Melanoma |
| | MC1R | Melanoma |
| | Prostate-pecific antigen | Prostate |
| Mutated | β-catenin | Melanoma, Prostate, HCC |
| | BRCA1/2 | Breast, ovarian carcinoma |
| | CDK4 | Multi |
| | CML66 | CML |
| | Fibronectin | Multi |
| | MART-2 | Melanoma |
| | p53 | Multi |
| | Ras | Multi |
| | TGF-βRII | Colorectal carcinoma |
| Posttranslationally altered | MUC1 | Ductal carcinoma, RCC |
| Idiotypic | Ig, TCR | B, T leukemia, lymphoma, myeloma |

BRCA = breast cancer antigen;
CDK4 = cyclin-dependent kinase-4;
CEA = carcino-embryonic antigen;
CML66 = chronic myelogenous leukemia (antigen) 66;
CT = cancer testis;
HPV = human papilloma virus;
Ep-CAM = epithelial cell adhesion molecule;
Ig = immunoglobulin;
MART-1/-2 = melanoma antigen recognized by T cells-1/-2;
MC1R = melanocortin-1-receptor;
SAP-1 = stomach cancer-associated protein tyrosine phosphatase-1;
TAG-72 = tumor antigen-72;
TCR = T cell receptor;
TGF-βRII = transforming growth factor-β receptor II;
TRP = tyrosinase-related protein.

(From: Categories of Tumor Antigens, Holland-Frei Cancer Medicine. 6th edition., Kufe D W, Pollock R E, Weichselbaum R R, et al., editors. Hamilton (ON): BC Decker; 2003. Copyright© 2003, BC Decker Inc).

One embodiment provides a composition comprising a compound of formula I or a pharmaceutically acceptable salt thereof as described herein, which further comprises a first dihydrofolate reductase (DHFR) molecule linked to second DHFR molecule via a linker.

One embodiment provides a composition comprising a compound of formula I or a pharmaceutically acceptable salt thereof as described herein, which further comprises a first dihydrofolate reductase (DHFR) molecule linked to second DHFR molecule via a linker wherein the first dihydrofolate reductase (DHFR) molecule linked to second DHFR molecule via a linker further comprises a targeting molecule.

One embodiment provides a composition comprising a compound of formula I or a pharmaceutically acceptable salt as described herein, further comprising (a) a first dihydrofolate reductase (DHFR) molecule linked to second DHFR molecule via a linker wherein the first dihydrofolate reductase (DHFR) molecule linked to second DHFR molecule via a linker further comprises a targeting molecule and (b) a cell capable of inducing apoptosis.

One embodiment provides a composition comprising a compound of formula I or a pharmaceutically acceptable salt as described herein, further comprising (a) a first dihydrofolate reductase (DHFR) molecule linked to second DHFR molecule via a linker and (b) a cell capable of inducing apoptosis.

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I or conjugates of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the compounds or conjugates may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the compounds or conjugates may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compounds or conjugate in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The compounds or conjugates may also be administered intravenously or intraperitoneally by infusion or injection. Solutions of the active compounds or conjugates or salts thereof can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the compounds or conjugates in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Certain embodiments of the invention will now be illustrated by the following non-limiting Examples.

Example 1

Materials and Methods

DHFR$^2$antiEpCAM protein was prepared according to previously described methods (Li, Q., et al., Design and Characterization of an Anti-CD3 IgM Biomimetic. JACS, 2010. 132: p. 17247-17257). Detailed experimental procedures for plasmid reconstruction is described elsewhere. The lipid-bisMethotrexate was prepared using an earlier generation amine-based dimerizer, which had been modified to contain a free thiol moiety. Through a maleimide coupling the phospholipid-PEG moiety was appended onto the terminal end of the dimerizer. DHFR$^2$antiEpCAM LCSANs were assembled using a three-fold excess of dimerizer to DHFR protein. Oligomerization was monitored through size-exclusion chromatography.

Activated T-cells were obtained through density gradient centrifugation, followed by activation with Dynabeads® Human T-activator CD28+/CD3+ beads (Life technologies) and 0.5 μg/mL MCF-7 and U87 adherant cell lines were grown in RPMI media supplemented with 10% FBS, 2 mM L-glutamine and 1 mM Penicillin/Streptomycin antibiotics. Fluorescent confocal microscopy images were obtained using an Olympus FluoView FV 1000 BX2 Upright Confocal Microscope, and time-lapse confocal images were obtained using a Nikon BioStation IM imaging system. Cell lysis experiments were done using the CytoTox96® Non-Radioactive Cytotoxicity Assay kit (Promega).

A. Synthetic Methods

Synthesis of BisMTX-PEG-Thiol-Trilinker Methyl Ester (1a):

To a solution of bisMTX-NH2 trilinker (Fegan, A., et al., Chemically self-assembled antibody nanostructures as potential drug carriers. Mol. Pharmeceutics, 2012. 9: p. 3218-3227) (1) (65.0 mg, 53.30 μM), Thiol-dPEG(4) (18.0 mg, 63.95 μM) and HOBt (16.25 mg, 106.6 μM) in anhydrous DMF (5 mL), DIC (13.45 mg, 16.7 μL, 106.6 μM) was added under Ar. The reaction mixture, under continuous Ar flow, was stirred at room temperature for 24 hrs in the dark. After evaporation of the solvent, the residue was dissolved in water and a few drops of acetonitrile and purified by reverse phase flash chromatography employing ACN/0.1% TFA and Water/0.1% TFA as mobile phase using C18-SepPak cartridge column and lyophilized to obtain the product (1a) as yellow powder (77.0 mg, 97%). ESI-MS for $C_{69}H_{102}N_{20}O_{15}S$, [m/z] calcd. 1482.7654. found 1482.7509.

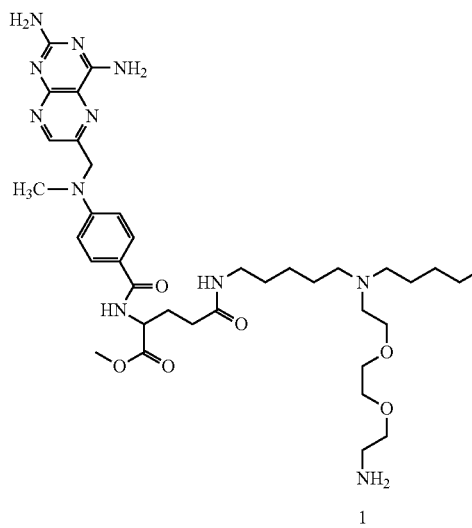
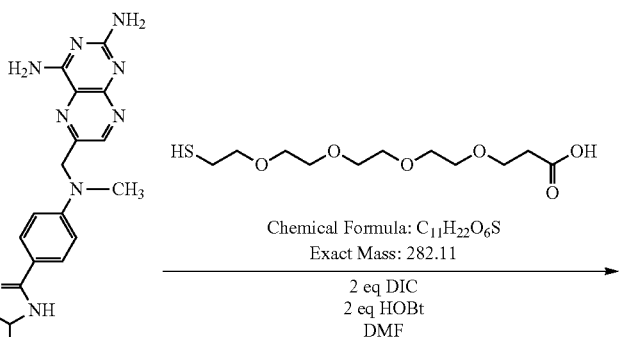

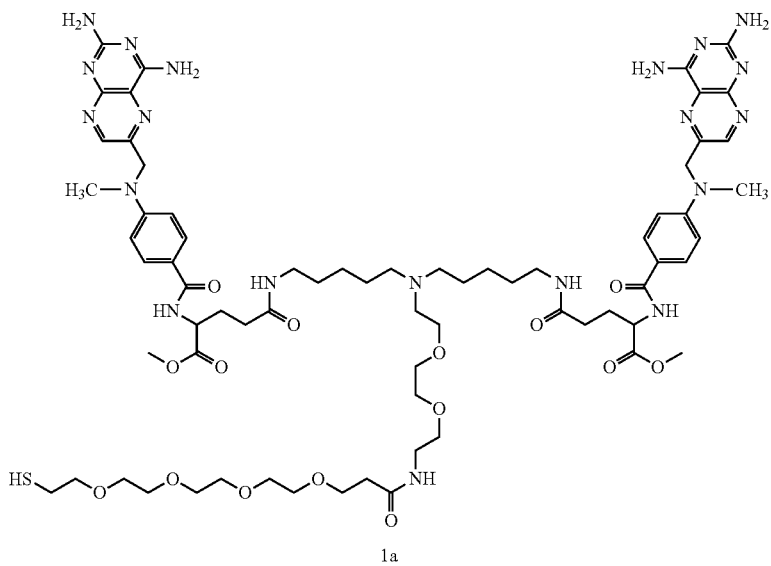

Synthesis of BisMTX-PEG-Thiol-Trilinker (2):

Lyophilized bisMTX-PEG-thiol-trilinker methyl ester (1a) (77.0 mg) was dissolved in ethanol (2 mL) and water (1 mL) and treated with 0.3 mL of 2N NaOH. Slow stirring was continued for 3 hrs at room temperature in the dark. The reaction mixture was further treated with 100 equivalent of DTT for 2 hrs in the dark and purified by reverse phase flash chromatography employing ACN/0.1% TFA and Water/0.1% TFA as mobile phase using C18-Sep-Pak cartridge column and lyophilized to obtain the bisMTX-PEG-thiol-trilinker (2) as yellow powder (40.0 mg, 53%). ESI-MS for $C_{67}H_{98}N_{20}O_{15}S$, [m/z] calcd. 1454.7241. found 1454.7068.

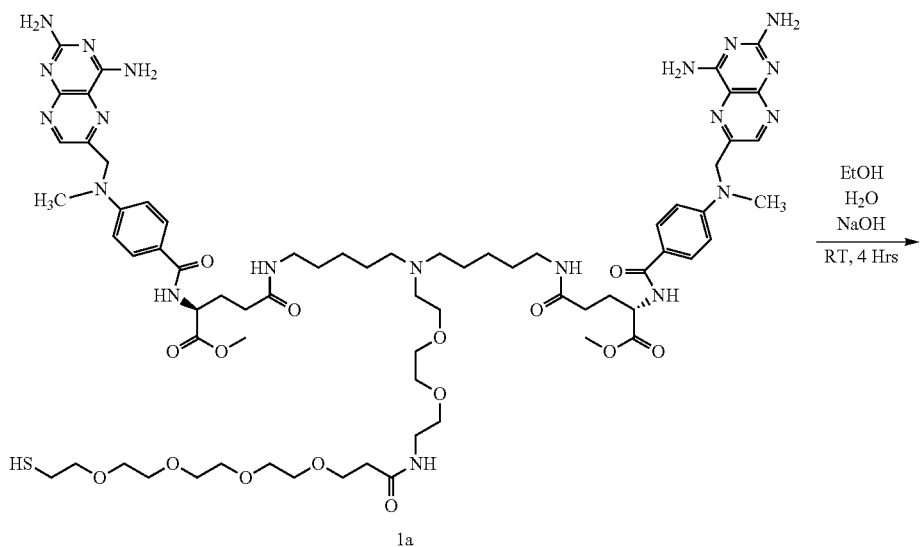

1a
Chemical Formula: $C_{69}H_{102}N_{20}O_{15}S$
Exact Mass: 1482.7554

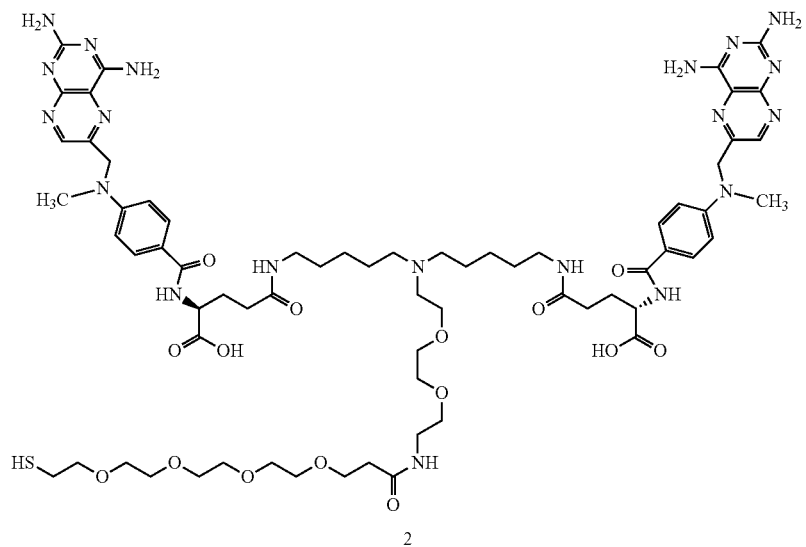

2
Chemical Formula: $C_{67}H_{98}N_{20}O_{15}S$
Exact Mass: 1454.7241

Synthesis of BisMTX-PEG-DSPE Trilinker (P-PEG-bis-MTX):

Commercially obtained DSPE-PEG(2000)-Maleimide (Avanti Polar Lipids, Inc.) (10.0 mg, 3.4 µM) and bisMTX-PEG-thiol-trilinker (2) (9.90 mg, 6.80 µM) were dissolved in TE buffer (Tris-Cl 10 mM, EDTA 1.0 mM, pH 7.0). A small amount of DMF (0.6 mL) was added to increase the solubility and slow stirring was continued at room temperature for two days in the dark. The solvents were removed under reduced pressure. The residue was dissolved in a small amount of 50% acetonitrile in water and purified by reverse phase flash chromatography using ACN/0.1% TFA and Water/0.1% TFA as a mobile phase employing a C18-Sep-Pak cartridge column, followed by lyophilization to obtain the product as a yellowish white powder. ESI-MS for $C_{206}H_{365}N_{23}O_{72}PS$, [m/z] calcd. 4377.5149. found 4377.6784.

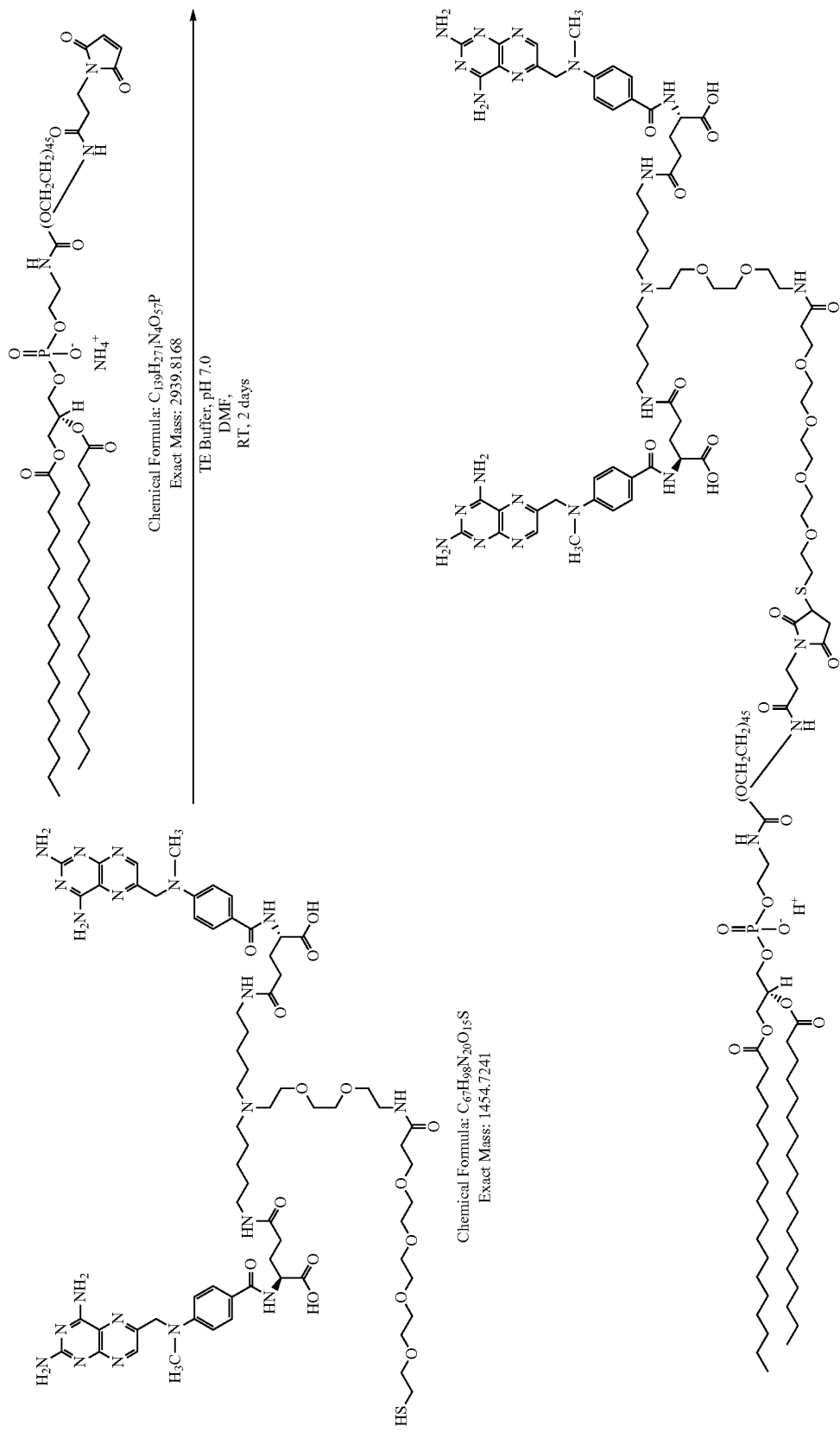

B. Oligomerization and Size Exclusion Analysis of Lipid CSANs

Figure 5:
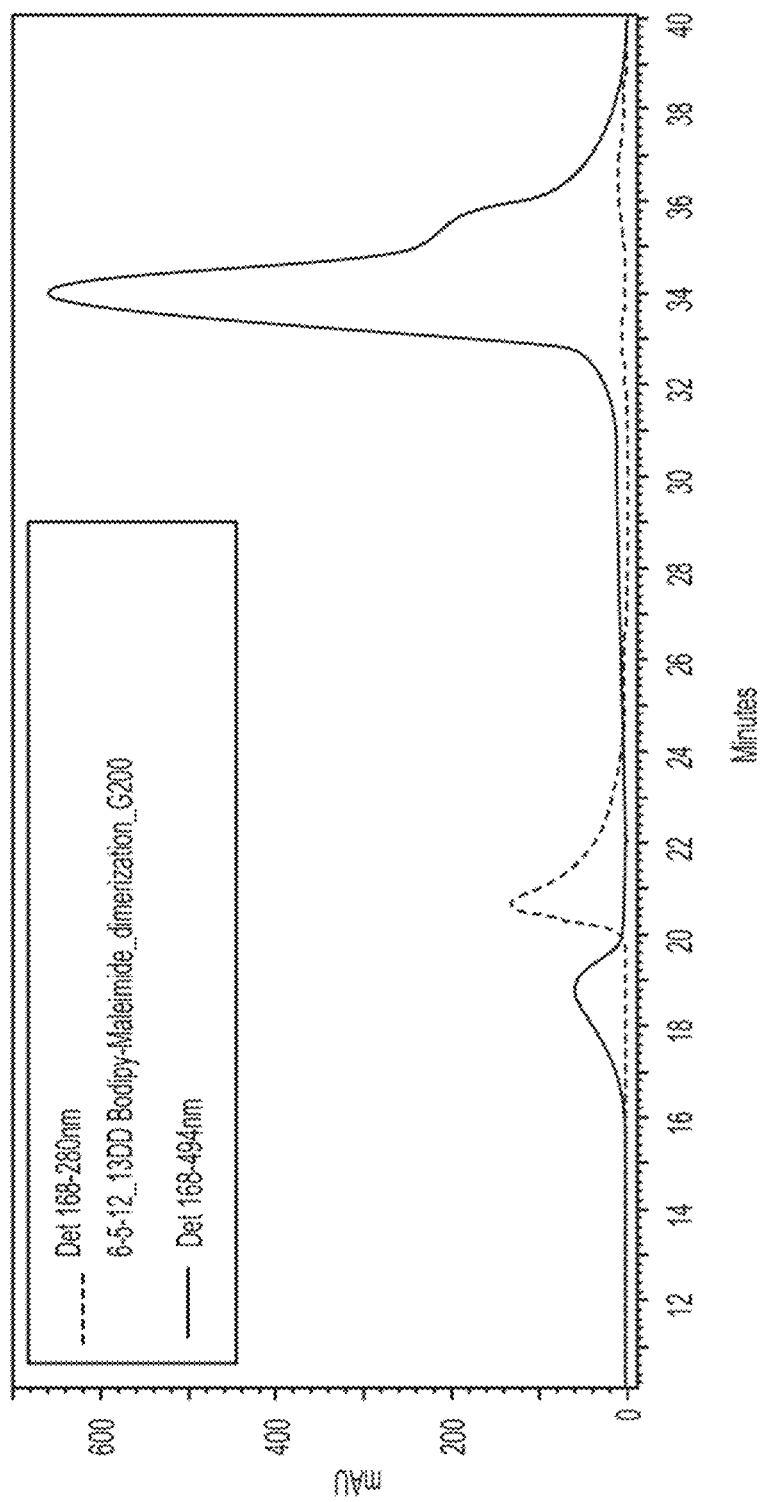
FIG. 5 shows the size exclusion chromatography spectra of oligomerized 13DHFR2Bodipy protein. Black (higher trace on right hand side) trace corresponds to monomeric protein prior to oligomerization with P-PEG-bisMTX. Lower trace on left hand side corresponds to multimeric protein species formed following combination of the 13DHFR2Bodipy protein and the P-PEG-bisMTX dimerizer.

One equivalent of the purified fusion protein 13DHFR²Bodipy was allowed to incubate with three equivalents of the bisMTX-PEG-DSPE Trilinker for one hour at room temperature in P500 buffer (0.5M NaCl, 50 mM $KH_2PO_4$, 1 mM EDTA, pH 7). Following incubation, the oligomerized samples were injected onto a Superdex G200 column on an SEC-HPLC (Amersham Biosciences, USA) to observe the change in protein elution time from the previously injected monomer standard. (SEC 3) Protein was collected based upon retention times observed through absorbance at 280 nm (FIG. 5).

C. Confocal Microscopy

Figure 6:
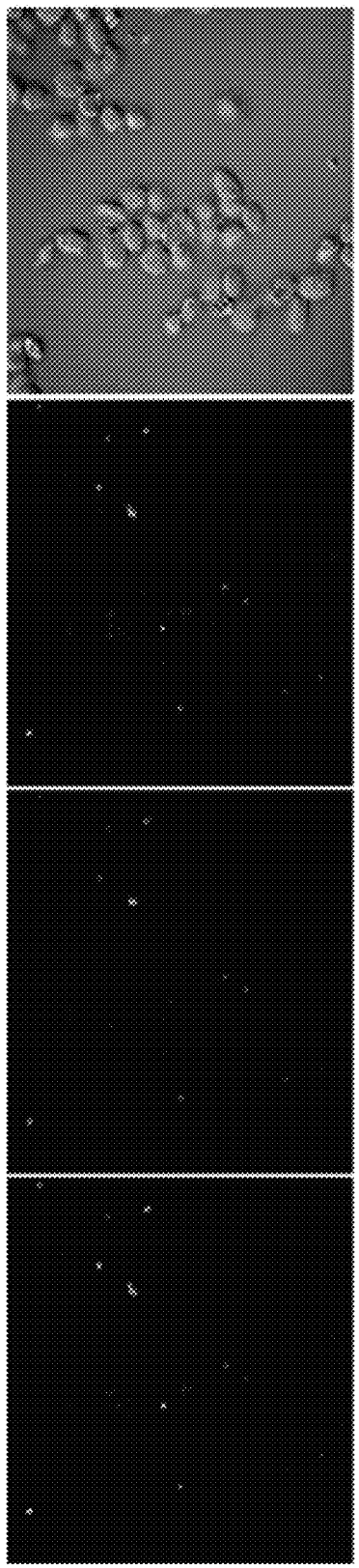
FIG. 6 shows the colocalization of DHFR$^2$-Bodipy LCSANs (1 µM) and AF594-CT-B. Left image shows Bodipy channel. Second image shows Alexafluor channel. Third image shows an overlay of the Bodipy and Alexafluor channels. Final image shows the overlay of the merged image on top of a phase contrast image.
Figure 7A:
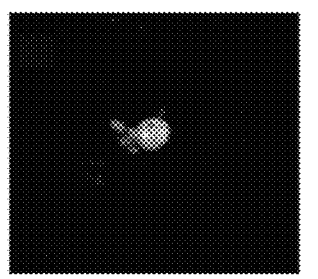
FIGS. 7A-I shows the treatment of HPB-MLT cells with 13DDBodipy lipid-CSANs.
Figure 7B:
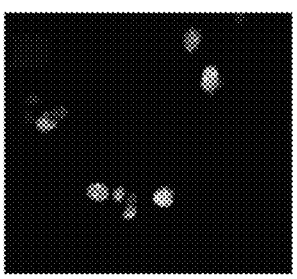
Figure 7C:
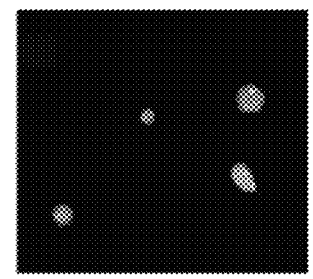
Figure 7D:
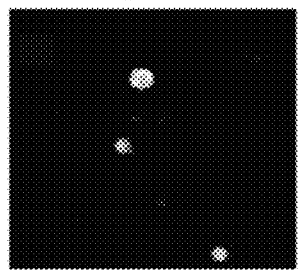
Figure 7E:
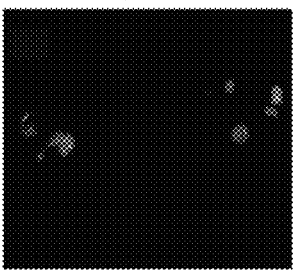
Figure 7F:
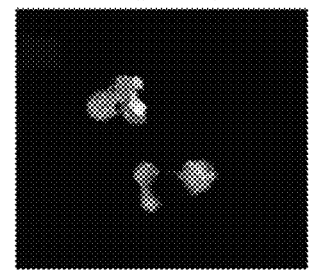
Figure 7G:
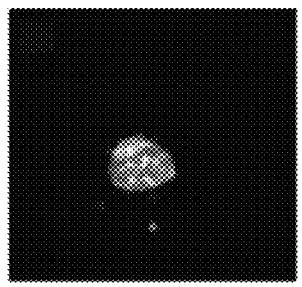
Figure 7H:
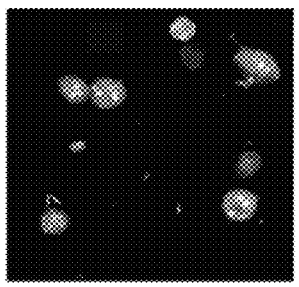
Figure 7I:
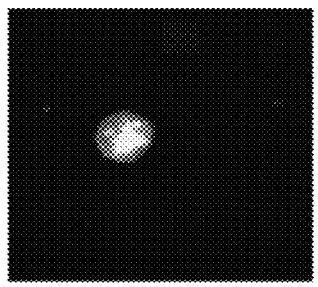

To prepare slides for confocal microscopy using the DDBodipy lipid-CSANs, HPB-MLT cells ($1\times10^6$ cells per well) were suspended into RPMI-1640 media (Gibco®) supplemented with 10% heat-inactivated fetal bovine serum, 100 μg/mL penicillin/streptomycin, and 2 mM L-arginine HPB-MLT cells were the treated with 1-5 μM of the DDBodipy lipid-CSANs, in a total of 200 μL of RPMI-1640 media. HPB-MLT cells were allowed to incubate at 37° C. for thirty minutes to seventy-two hours, at which time the cells were pelleted through centrifugation and the treatment was removed. For lipid colocalization experiments, XuM of AF594-CT-B was added 30 minutes prior to media removal. Cells were washed three times with 1 mL PBS buffer, and then fixed with 200 μL of a 4% paraformaldehyde solution for 15 minutes. The paraformaldehyde solution was removed, and the cells were again washed three times with 1 mL of PBS buffer. Following the final centrifugation the HPB-MLT cells were resuspended in 25 μL of PBS, and were allowed to air dry on Poly Prep Slides™ coated with poly-L-lysine (Sigma). Once dry, coverslips were then adhered to the glass slides using one drop of ProLong® Gold Antifade Reagent (Life technologies) containing DAPI. The slides were allowed to dry overnight in the absence of light to prevent bleaching of the fluorescent dyes. The following morning the slides were sealed using clear nail polish, and visualized using the Olympus FluoView FV 1000 BX2 Upright Confocal microscope in the University of Minnesota Imaging Centers (FIG. 6).

For sample preparation of the lipid-CSAN stability treatments, HPB-MLT cells ($1\times10^6$ cells in 100 μL) were treated with 1 μM of the 13DDBodipy lipid-CSANs. For media removal studies, cells were pelleted through centrifugation every thirty minutes. Media was removed and the cells were resuspended into fresh supplemented RPMI media. Previous to each centrifugation an aliquot of cells were fixed using a 4% paraformaldehyde solution and adhered to Poly Prep Slides™ coated poly-L-lysine slide using ProLong® Gold Antifade Reagent. For the extended time-point treatments, HPB-MLT cells ($1\times10^6$) were treated with 1 μM in 600 μL of supplemented RPMI media at 37° C. Every twenty-four hours up to a total of seventy-two hours 200 μL of cells were removed and fixed using a 4% paraformaldehyde solution and adhered to Poly Prep Slides™ coated poly-L-lysine slide using ProLong® Gold Antifade Reagent (FIGS. 7A-I).

For preparation of slides using the antiEpCAM lipid-CSANs to induce cell-cell interactions, 2 mL of MCF-7 cells ($1\times10^5$ cells per well) in RPMI media supplemented with 10% heat-inactivated fetal bovine serum, 100 μg/mL penicillin/streptomycin, and 2 mM L-arginine were seeded into individual wells (containing a glass coverslip) of a six-well plate. Cells were then left to incubate overnight at 37° C. to allow cells to adhere to the glass coverslips. The following day, HPB-MLT cells were labeled with Carboxyfluorescein succinimidyl ester (CFSE, Invitrogen) according to the manufacturer's directions. Labeled HPB-MLT cells ($1\times10^6$ cells in 100 μL of supplemented RPMI media) were then treated with 0-1 μM of the antiEpCAM lipid-CSANs for one hour at room temperature. Following the initial incubation, HPB-MLT cells were then brought up to a volume of 1 mL in media, and were then added to each well of the 6-well plate. MCF-7 cells and HPB-MLT cells were then allowed to incubate together at 37° C. for one hour. Media was removed, and cells were washed twice with 1 mL PBS buffer. Cells were then fixed for 15 minutes in 200 μL of a 4% paraformaldehyde solution, and were again washed twice with 1 mL PBS buffer. Cells on the glass coverslips were allowed to air dry for approximately 30 minutes. Once dry, coverslips were then adhered to glass slides using ProLong® Gold Antifade Reagent containing DAPI (Invitrogen). Slides were allowed to dry overnight in the absence of light to avoid bleaching of incorporated dyes. Slides were viewed the following day using the Olympus FluoView FV 1000 BX2 Upright Confocal microscope in the University of Minnesota Imaging Centers.

D. Flow Cytometry Analysis

Stability studies were conducted using flow cytometric analysis. HPB-MLT cells ($5\times10^6$ in 200 μL of supplemented RMPI media, Gilco®) were treated with 0-1 μM of the 13DDBodipy lipid-CSANs and incubated at 37° C. in 5% $CO_2$ air supply conditions. After an incubation of one hour, cells were pelleted through centrifugation to remove excess lipid-CSANs. Prior to centrifugation, an aliquot of cells were removed and fixed using 4% paraformaldehyde for 15 minutes. Cells were washed once with 200 μL of PBS and were resuspended in a final volume of 200 μL of PBS. The remaining cells were again resuspended in 150 μL of supplemented RPMI media. This process was repeated every thirty minutes for a total of three hours. Fixed samples suspended in PBS were analyzed using a FACSCalibur flow cytometer (BD bioscience).

Figure 8:
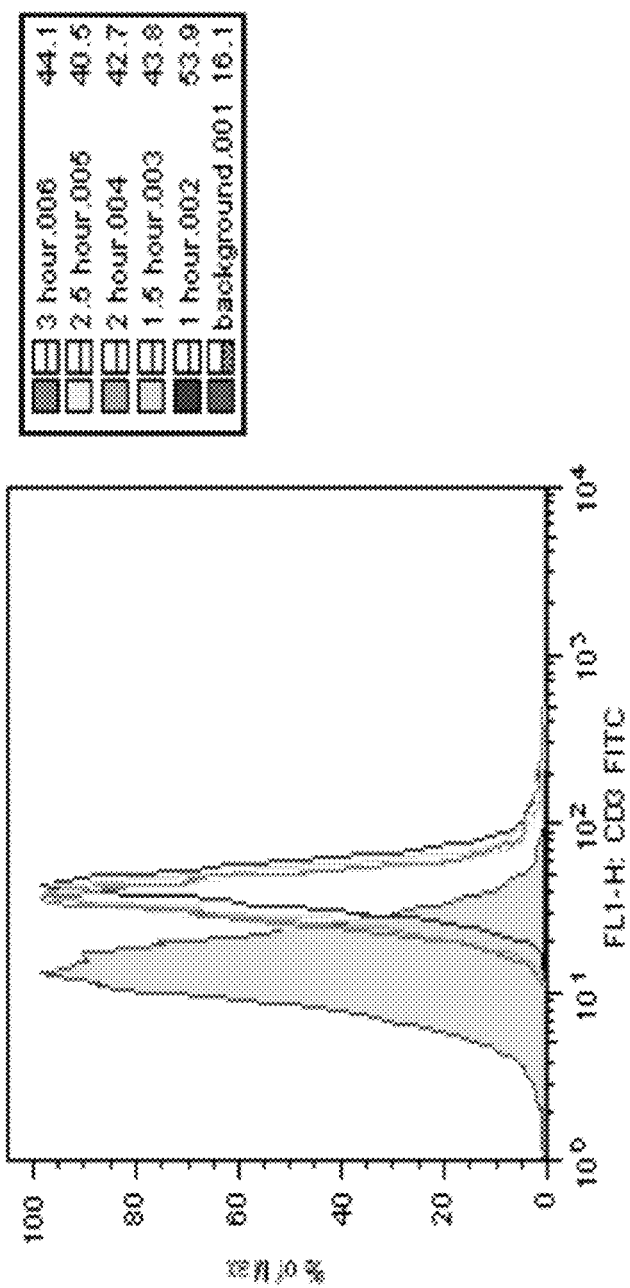
FIG. 8 shows the flow cytometry analysis of LCSAN stability. HPB-MLT cells were treated with 1 µM 1DHFR$^2$Bodipy Lipid nanorings for one hour. Following the initial incubation media was removed at half-hour intervals. Cells were fixed at each time point and were then analyzed using flow cytometry. The graphs from left to right are the background, 3 hr, 2.5 hr, 2 hr 1.5 hr and 1 hr interval graphs.
Figure 9A:
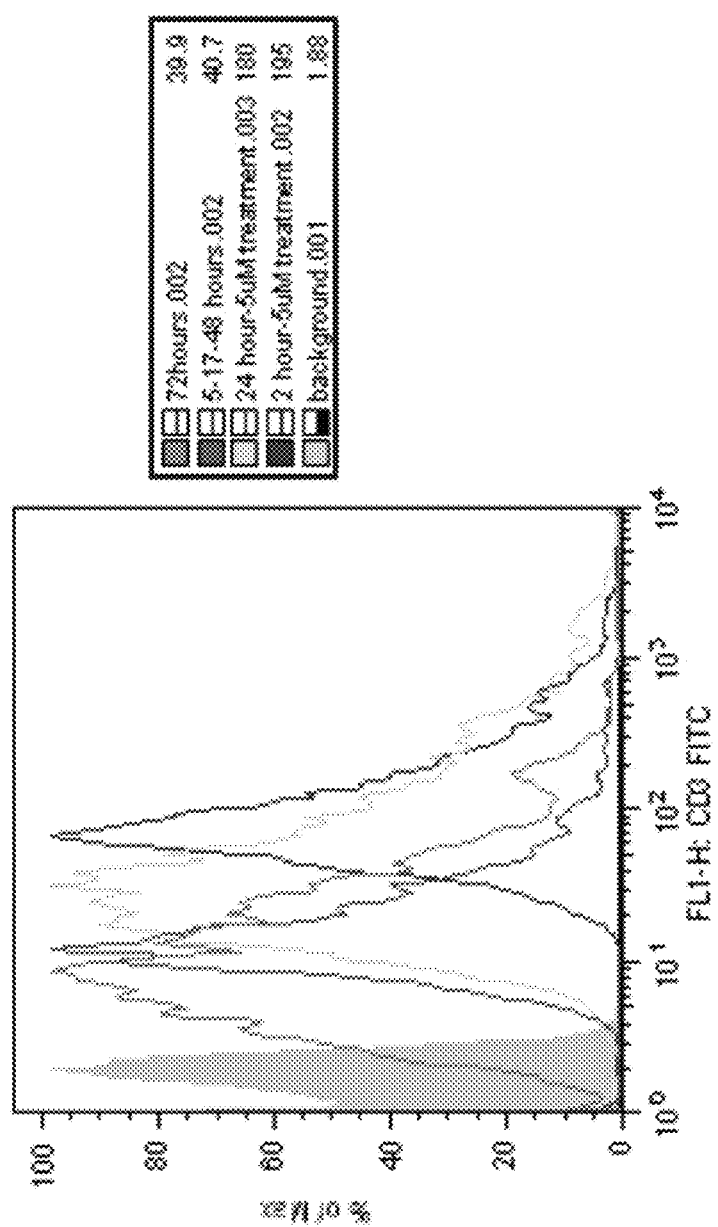
FIG. 9A shows the flow cytometry analysis of LCSAN stability. HPB-MLT cells were treated with 5 µM 1DHFR$^2$Bodipy Lipid nanorings for two hours, and were then analyzed using flow cytometry at 24, 48 and 72 hours after removal of the nanoring treatment. The graphs from left to right are the background, 72 hr, 48 hr, 24 hr and 2 hr graphs.

Stability studies conducted over seventy-two hours were done using HPB-MLT cells ($5\times10^6$ in 600 μL of supplemented RPMI media, Gilco®) treated with 0-1 μM of the 13DDBodipy lipid-CSANs and incubated at 37° C. in 5% $CO_2$ for seventy-two hours. 200 μL aliquots were removed every twenty-four hours, were pelleted through centrifugation and were resuspended in 200 μL of PBS. Cells were analyzed using a FACSCalibur flow cytometer (BD bioscience) (FIG. 8, FIG. 9A).

E. Trimethoprim Release

Dissociation of cell-cell interactions was imaged using confocal microscopy techniques. MCF-7 cells ($1\times10^5$ cells in 1 mL of supplemented DMEM media, Gilco®) were plated into each well of a 6-well plate that contained a glass coverslip. MCF-7 cells were allowed to adhere to the coverslip overnight at 37° C. supplemented with 5% $CO_2$. The following day HPB-MLT cells ($2\times10^6$ cells) were stained with Carboxyfluorescein succinimidyl ester (CFSE, Invitrogen) according to the manufacturer's directions. Stained HPB-MLT cells were treated with 1 μM of the 13DDantiEpCAM and 1DDantiEpCAM lipid-CSANs for one hour at 37° C. Following the initial incubation, HPB-MLT cells were added to the MCF-7 cells at a 10:1 ratio in 1 mL of DMEM media. The cells were allowed to incubate for one hour at 37° C., and were then washed three times using 1 mL PBS. The coverslips were then broken in half and placed into two separate wells, and were then treated with either DMEM media, or DMEM media containing 20 μM trimethoprim. The cells were allowed to incubate for an additional two hours upon which time they were washed three times with 1 mL of PBS, and were then fixed using a solution of 4% paraformaldehyde for 15 minutes. After fixing the cells they were again washed three times with PBS and were dried and adhered to glass slides using ProLong Antifade® reagent containing DAPI (Invitrogen).

TABLE S1

|   | 13DDEpCAM | 20 uM TMP 13DDEpCAM | 1DDEpCAM | 20 uM TMP 1DDEpCAM |
|---|---|---|---|---|
| 1 | 77 | 4 | 66 | 7 |
| 2 | 51 | 2 | 67 | 21 |
| 3 | 51 | 3 | 56 | 14 |
| 4 | 32 | 11 | 68 | 1 |
| 5 | 40 | 11 | 41 | 5 |
| Average | 50 | 6.2 | 60 | 9.6 |
| St dev | 17 | 4.4 | 11 | 7.9 |

Quantitative results from confocal microscopy trimethoprim release experiments. Five different views were analyzed for the number of HPB-MLT cells remaining attached to the confocal slide.

F. Non-Radioactive Cytotoxicity Assay

Figure 9B:
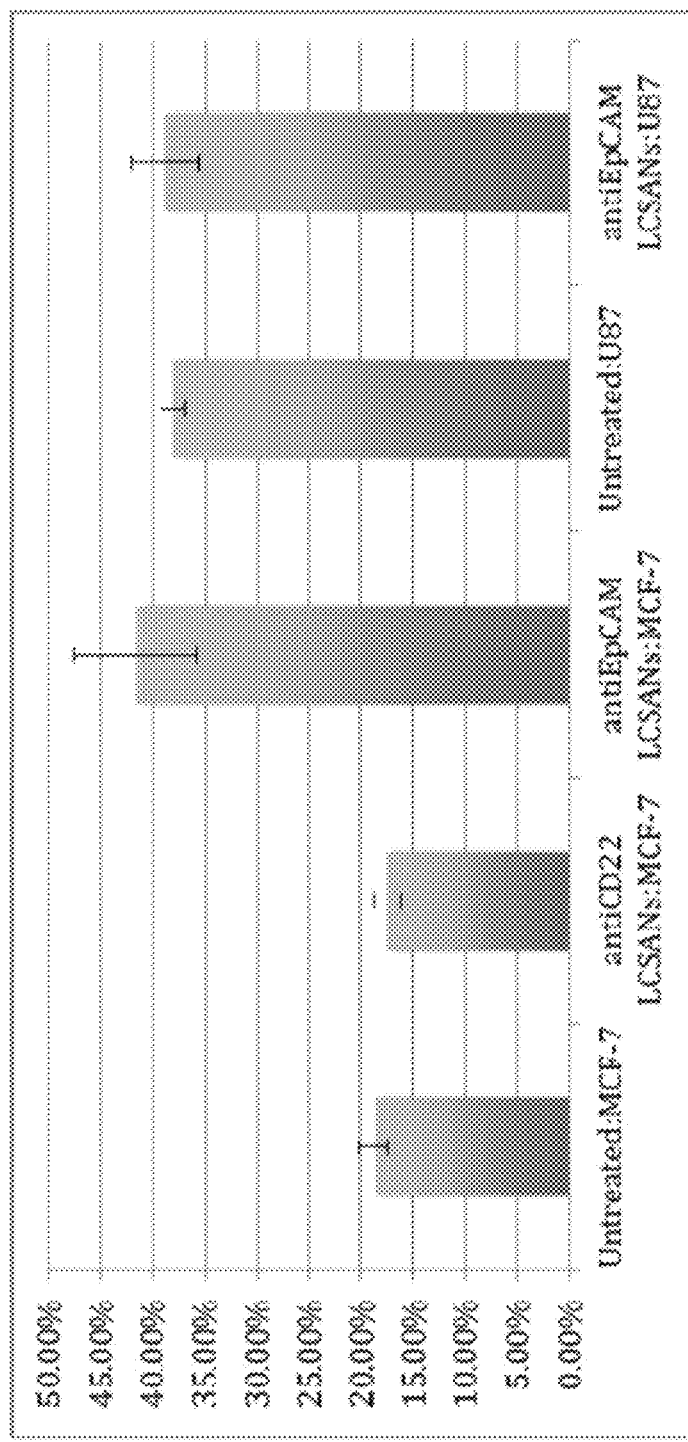
FIG. 9B shows the control cell lysis experiments. Control experiments were done using a 10:1 effector to target ratio. Results are shown as treatment type:cell line. Results show that MCF-7 cells treated with T-cells reengineered with irrelevant LCSAN control do not show additional cell killing when compared to untreated controls. U87, EpCAM-cell line shows no additional cell lysis when treated with anti-EpCAM LCSAN reengineered T-cells as compared with untreated controls.

Measurement of cytotoxicity of MCF-7 cells upon incubation with treated or untreated T cells was done using a non-radioactive cytotoxicity assay (CytoTox 96® Non-Radioactive Cytotoxicity Assay, Promega) that measures the amount of lactate dehydrogenase (LDH) enzyme is present following cell lysis. The day previous to the experiment 5,000 MCF-7 cells per well are seeded into a 96-well plate in 200 μL of RPMI-1640 media per well. The cells are allowed to adhere to the plate overnight in a 37° C. incubator supplemented in 5% $CO_2$. The following day resting or activated (CD3/CD28, IL2) PBMCs are counted and incubated with 0-2.5 μM of the antiEpCAM lipid CSANs for one hour at 37° C. with 5% $CO_2$. Following the initial incubation, treated or untreated PBMCs are added to each well at E:T ratios ranging from 1:1 to 50:1. The cells are allowed to incubate for four hours at 37° C. with 5% $CO_2$. Forty-five minutes prior to the end of the four-hour incubation 20 μL of lysis buffer was added to three wells that correspond to the max lysis of only MCF-7 cells. At the end of the four-hour incubation the plate was removed from the incubator and centrifuged at 250×g for four minutes. Following centrifugation, 50 μL was removed from each well and placed into a respective well in a second 96-well plate. An additional 50 μL of substrate mix was added to each well and the plate was allowed to incubate at room temperature in the dark for forty-five minutes. The reaction was stopped by adding 50 μL of the stop buffer included in the kit, and the absorbance of each well was read at 490 nm. Data was corrected for media absorbance, and values were determined according to the following equation (FIG. 9B):

$$\% \text{ Cytotoxicity} = \left( \frac{\text{Experimental} - \text{TargetSpontaneousRelease}}{\text{TargetMaxRelease} - \text{TargetSpontaneousRelease}} \right)$$

G. Time-Lapse Microscopy

Observation of cell-cell interactions and resulting cell lysis was observed over a twenty-hour period using time-lapse microscopy techniques. $6 \times 10^4$ MCF-7 and U87 cells (previously conjugated with the PKH26 fluorescent dye) were plated into each well of a four-well 35 mM culture dish (Quad Divided 35 mm Ibidi Chamber Dish Hi-Q4, Nikon Instruments Inc.) and allowed to adhere to the plate overnight. The following day resting or activated PBMCs ($3 \times 10^4$) were allowed to incubate with 0.5 μM of the antiEpCAM-antiCD3 bispecific CSANs, and were then added into the respective wells of the four-well culture dish. Samples were then placed into a Biostation IM cell incubator (Nikon Inc.) for imaging in a controlled environment of 37° C. with a 5% $CO_2$ air supply. Images were then taken over the course of twenty hours.

H. Differential Scanning Calorimetry of (DSC)

Figure 10A:
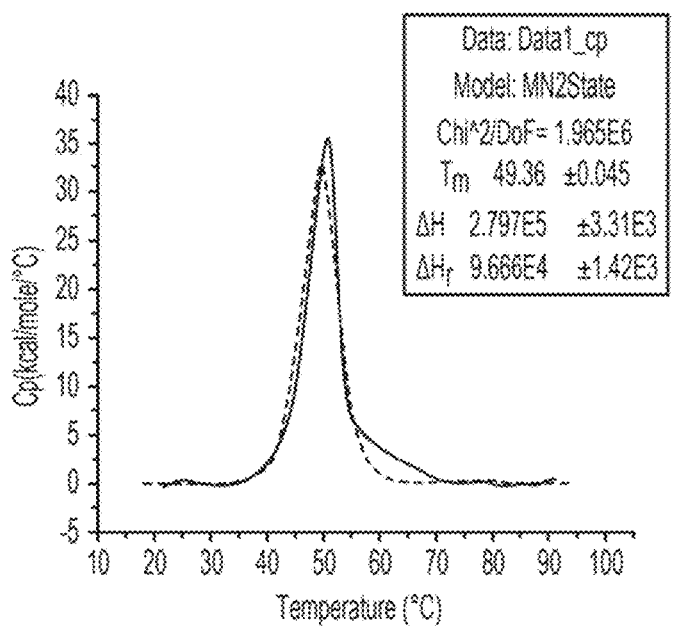
FIGS. 10A-C shows the DSC traces for, FIG. 10A) 13DHFR$^2$ monomer, FIG. 10B) 13DHFR$^2$ dimer, and FIG. 10C) 1DHFR$^2$ octamer.
Figure 10B:
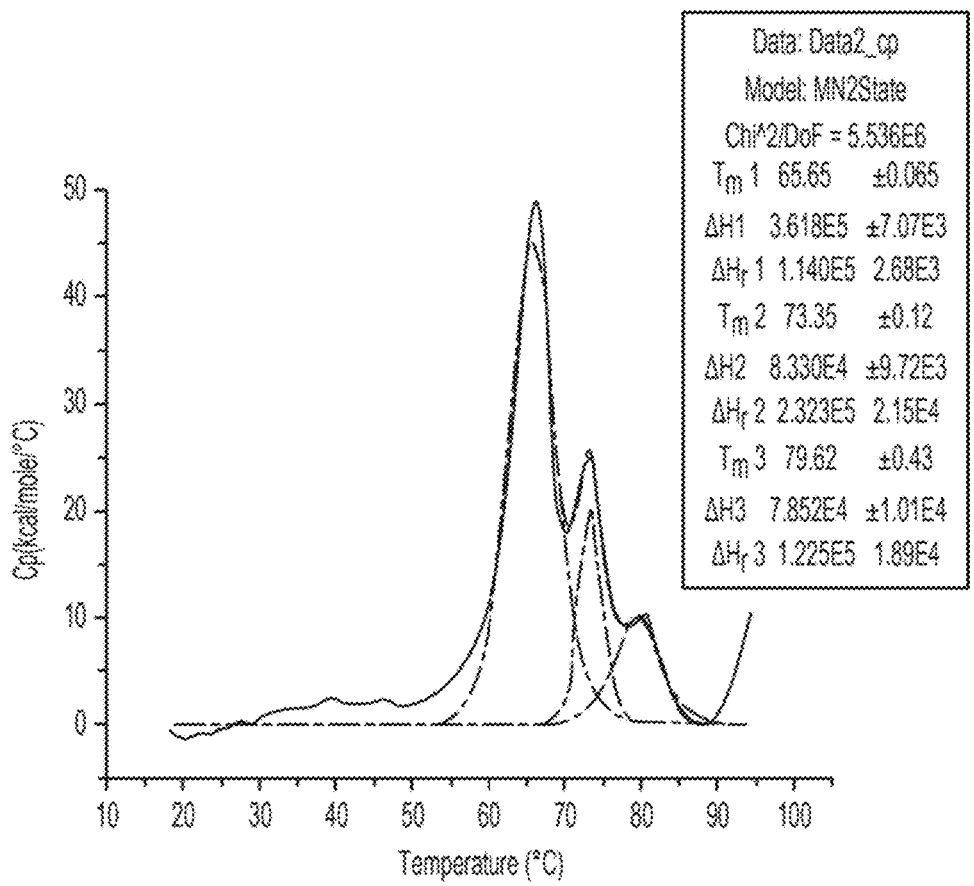
Figure 10C:
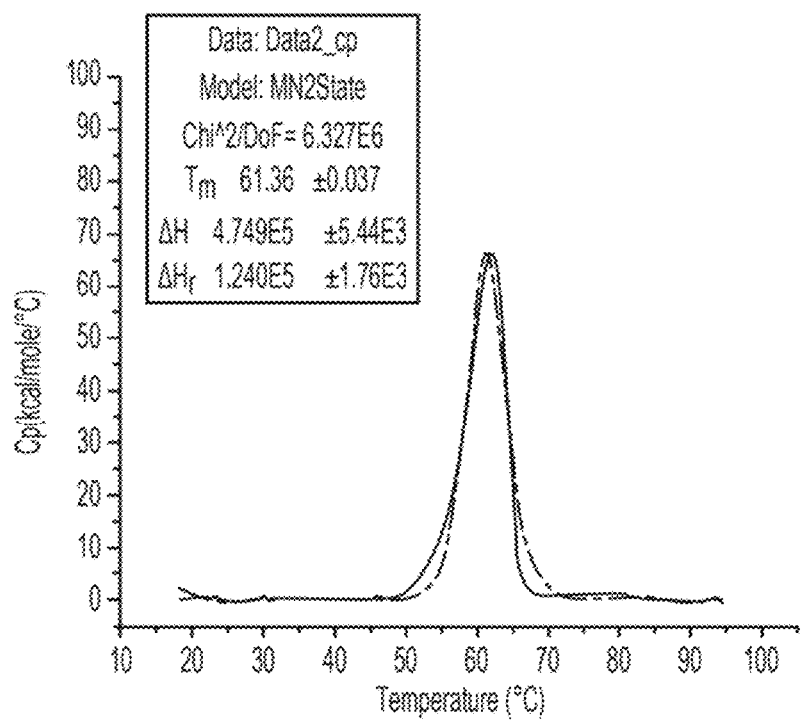

The proteins were dialyzed against a 0.2M $K_3PO_4$, 0.25M KCl buffer at pH 6.2, and diluted to a concentration of 1 mg/mL. Scans were performed using a VP-capillary DSC (MicroCal, LLC). Protein solutions were sampled from 96-well plates using the robotic attachment. Two scans were performed for baseline subtraction. Scans ran from 20-95° C. at 1° C./min using the medium feedback mode. Scans were analyzed using Origin 7.0. Nonzero baselines were corrected using a third order polynomial. The unfolding transitions of each antibody were fit using the non-two-state unfolding model within the software (FIGS. 10A-C).

TABLE S2

| Protein | Tm (° C.) |
|---|---|
| 13DHFR$^2$ Monomer | 49.36 ± 0.045 |
| 13DHFR$^2$ Dimer | 65.65 ± 0.065 |
| 1DHFR$^2$ Octomer | 61.36 ± 0.037 |

I. Plasmid Construction and Expression of DHFR$^2$-anti-CD22

Figure 11:
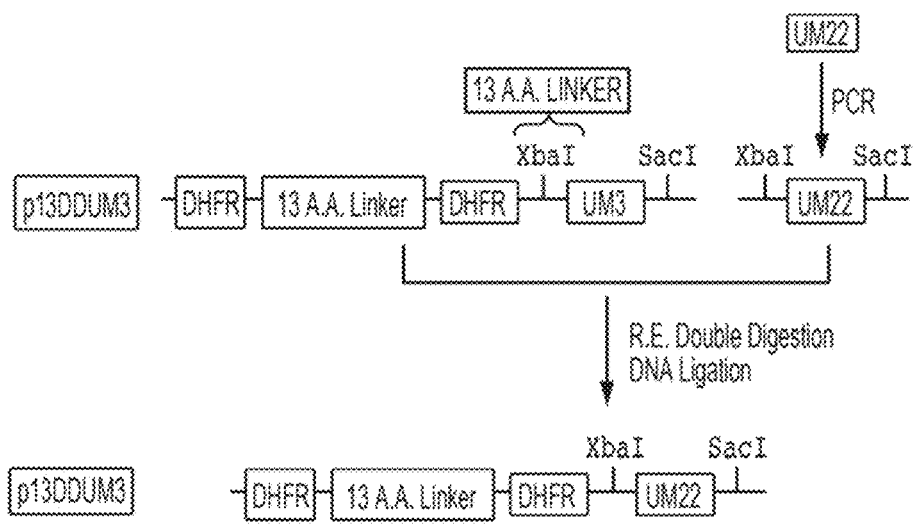
FIG. 11 shows the 13-DHFR2-anti-CD22 expression plasmid construction.

The plasmid expressing the antiC22 linked to a DHFR-13amino acid-DHFR through a 13 amino acid linker (p13DHFR$^2$CD22) was prepared from the previously reported (Li, Q., et al. Design and Characterization of an Anti-CD3 IgM Biomimetic. JACS, 2010. 132: p. 17247-17257). p13DHFR$^2$CD3 as follows. The plasmid pAntiCD22 was a gift from Dr. Daniel Vallera, Dept. of Radiation Oncology, University of Minnesota. The anti-CD22 scFv gene was prepared by PCR reaction on pAntiCD22, which amplified the DNA with primers having a 5'-XbaI site (TCTAGA) and 3'-SacI site (GAGCTC). The PCR product and the plasmid p13DHFR$^2$CD3 were double digested first by restriction enzyme XbaI (Invitrogen, CA), then by SacI (New England Biolabs, MA), respectively. Double digestion result was confirmed by Agarose DNA gel. The digested products were immediately treated by T4 ligase (New England Biolabs, MA) to form the plasmid p13DHFR$^2$CD22 encoding DHFR2-anti-CD22 scFv's fusion protein. The whole sequence was verified by automated DNA sequencing results (FIG. 11). Protein expression was performed from BL21(DE3) cells as previously reported (Li, Q., JACS, 2010. 132: p. 17247-17257).

Results and Discussion

Figure 2:
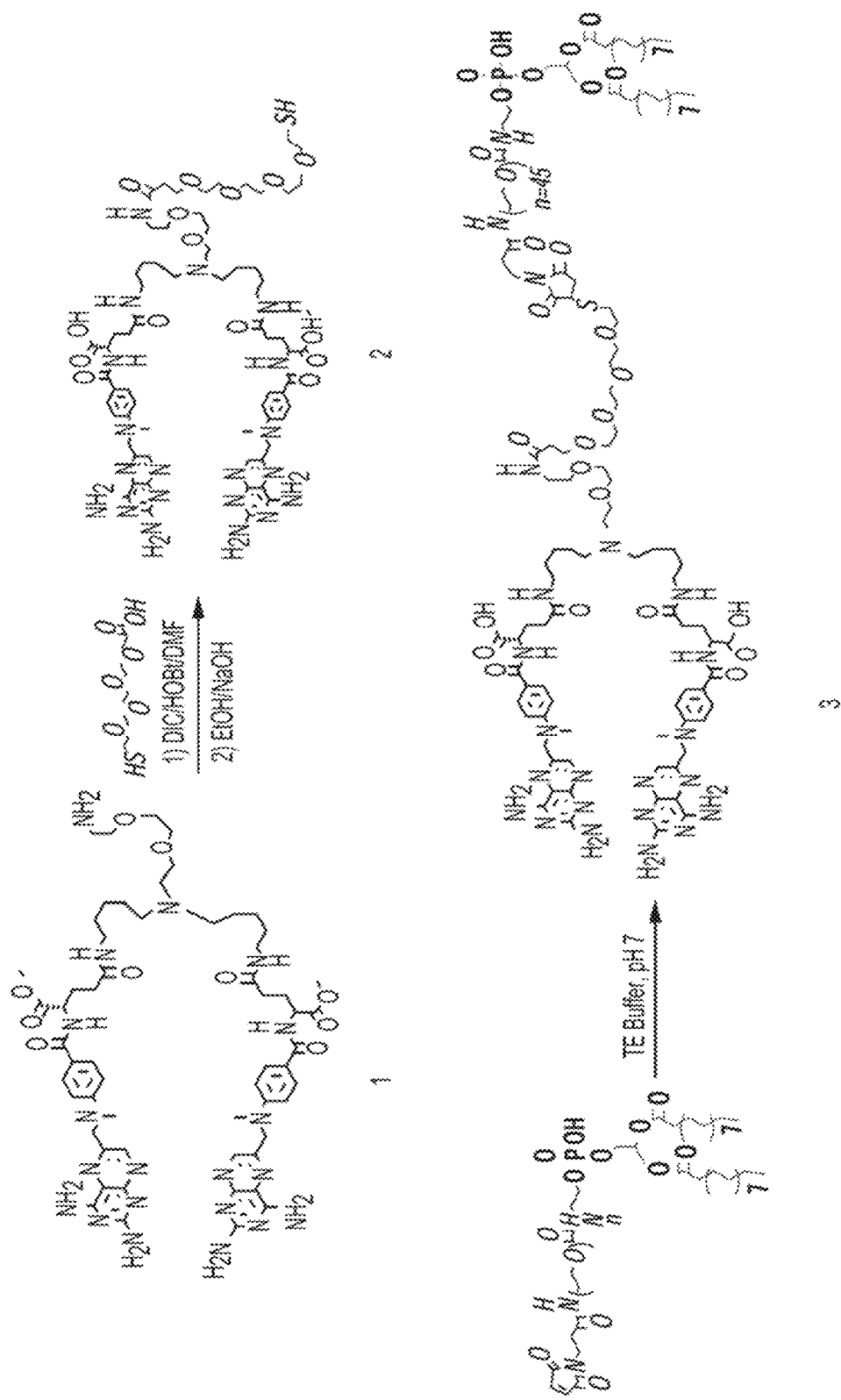
FIG. 2 outlines the synthesis of phospholipid-PEG-bis-methotrexate (P-PEG-bisMTX).

A phospholipid-PEG-bis-methotrexate (P-PEG-bisMTX) was prepared from the bis-MTX containing a free thiol (2)

which in turn was prepared from the protected trifunctional bis-MTX compound 1 (FIG. 2). Compound 2 was then conjugated to distearoyl phosphatidyl containing a PEG linker and a terminal maleimide in phosphate buffer, pH 7, yielding P-PEG-bisMTX. The combined length of the PEG linker was greater than 30 nM and thus would facilitate cell surface binding of the Lipid-CSANs, while the incorporation of distearoyl phosphotidyl choline would enable rapid and stable insertion into cell or liposomal membranes (Tokunaga, T., et al. Systematic Exploration of Lipophilic Tags That Allow Efficient Anchoring of Aptamers to Live Cell Surfaces. Chemistry Letters 42, 127-129, doi:10.1246/cl.2013.127, 2013).

DHFR2 proteins containing a thirteen amino acid linker (13-DHFR2) at an inserted C-terminal cysteine were fluorescently labeled with the dye, Bodipy. Incubation of each protein with P-PEG-bisMTX, as observed by size-exclusion chromatography (SEC), resulted in the predicted formation of the corresponding bivalent Lipid-CSANs (FIG. S2). The T-leukemia cell line, HPB-MLT, was then treated directly with the fluorescently labeled lipid CSANs. As can be seen from FIG. 3 A:I, the cell membranes were rapidly and uniformly labeled. When the concentration is lowered, the lipid CSANs were found to associate with distinct regions of the cell membrane that coincide with lipid raft staining. (FIG. S3) When labeled cells were washed hourly, no loss of the lipid CSANs was observed over the course of three and half hours. (FIG. S4) Over the course of 24, 48 and 72 h, confocal microscopy analysis revealed little or no loss of the lipid CSANs from the cell membrane following washing of the cells every 24 h. (FIG. S5) When quantitated by FACS analysis by measuring the mean fluoresence, an 8% loss of the lipid CSANs was observed over the first 24 h, followed by 80% loss over the next 24 h (48 h) and no appreciable loss over the final 24 h (72 h). (FIG. S6) Since the binding thermodynamics of the Lipid-CSANs to the membrane should not vary with time, the effect of dilution due to cellular division is likely the reason for the observed lower concentration of the observed Lipid-CSANs on the cell surface over this time period, as well at the heterogeneity of lipid raft formation.

To investigate the ability of Lipid-CSANs to not only modify the cell surface but also direct cell-cell interactions, we chose to prepare Lipid-CSANs capable of targeting the cancer antigen epithelial cell adhesion molecules (EpCAM). Epithelial cell adhesion molecules (EpCAM) are single transmembrane glycoproteins that are involved in the regulation of cell-cell adhesion and are over-expressed on a number of epithelial cancers, including colorectal, pancreatic, liver, ovarian and breast cancer. In addition, cancer stem cells have been shown to express EpCAM. We therefore chose to extend our approach by fusing an anti-EpCAM scFv to both 1-DHFR2 and 13-DHFR2. These proteins were then treated with P-PEG-bisMTX, thus forming anti-EpCAM bivalent and multivalent Lipid-CSANs (anti-EpCAM-Lipid-CSANs). The ability of HPB-MLT cells treated with anti-EpCAM-Lipid-CSANs to bind to the EpCAM positive breast cancer cell line, MCF-7 was then determined. As can be seen from FIG. 3 A:II-IV, after washing, untreated HPB-MLT cells did not adhere to MCF-7. However, based on cell image analysis 50 and 70-fold more HPB-MLT cells treated with either the bivalent and octavalent anti-EpCAM CSANs, respectively, were found bound to MCF-7 cells after washing. (Table S1, FIG. 3 I, III) Further analysis revealed that the anti-EpCAM-Lipid-CSANs treated HPB-MLT cells tended to be found associated with cell junctions, which are known to be EpCAM rich (Gostner J. M., et al. Effects of EpCAM Overexpression on Human Breast Cancer Cell Lines. BMC Cancer 11, 1-14, 2011).

Previously it was shown that upon the addition of excess trimethoprim, a non-toxic competitive inhibitor of DHFR, CSANs can undergo rapid extracellular and intracellular disassembly (Li, Q., et al. Self-Assembly of Antibodies by Chemical Induction. Angewandte Chemie-International Edition 47, 10179-10182, doi:10.1002/anie.200803507, 2008; Li, Q. et al. Chemically Self-Assembled Antibody Nanorings (CSANs): Design and Characterization of an Anti-CD3 IgM Biomimetic. J. Amer. Chem. Soc. 132, 17247-17257, doi:10.1021/ja107153a, 2010; Fegan, A., et al. R. Chemically self-assembled antibody nanostructures as potential drug carriers. Mol. Pharmeceutics 9, 3218-3227, 2012). To determine if the HBP-MLT cells treated with anti-EpCAM-Lipid-CSANs could be released when bound to MCF-7 cells, we incubated HPB-MLT cells that had been functionalized with anti-EpCAM-Lipid-CSANs and bound to MCF-7 cells with a twenty fold excess of trimethoprim for 2 hours. As can be seen in FIG. 3 B:II, IV, cells bearing both the bivalent and multivalent anti-EpCAM-Lipid-CSANs were released from the MCF-7 cells. resulting in a loss of approximately 85% of the HPB-MLT cells over this time period. (Table S1)

Figure 4A:
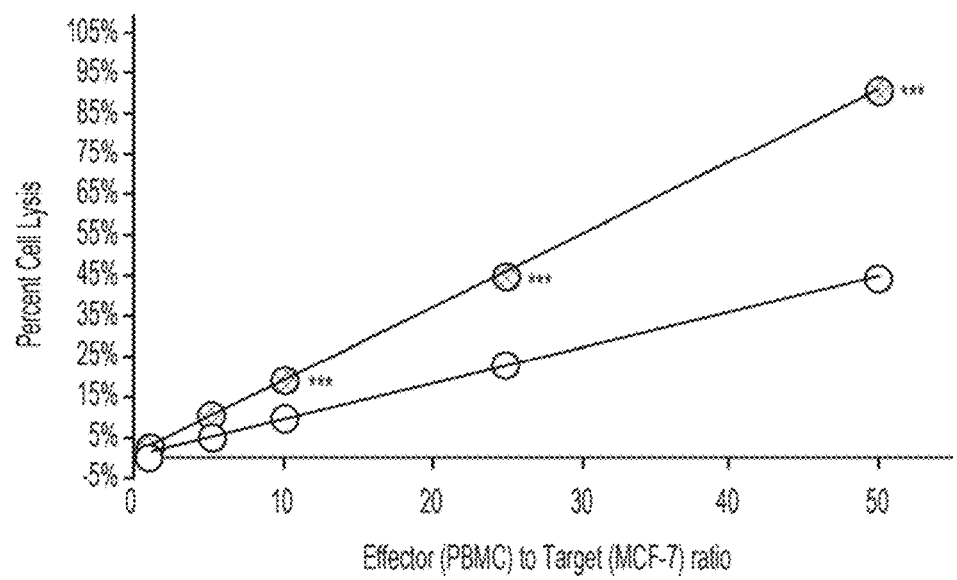
FIGS. 4A-C shows the redirected cell lysis of tumor cells upon incubation with anti-EpCAM Lipid-CSANs modified T-cells.
Figure 4B:
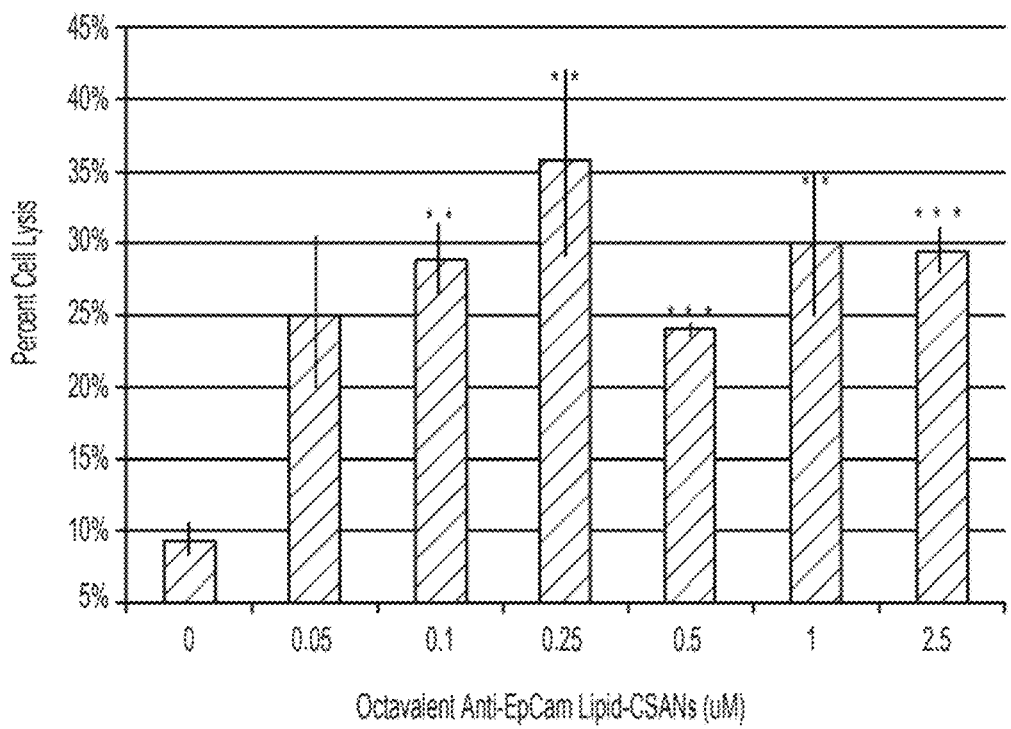

Following initial success redirecting anti-EpCAM-Lipid-CSANs modified HPB-MLT cells towards MCF-7 cells the methodology was then applied toward directing T-cells to induce target cell apoptosis. Activated PBMCs were first treated with anti-EpCAM-Lipid-CSANs (1 uM) for two hours, centrifuged to remove excess anti-EpCAM CSARs and incubated with MCF-7 cells at various ratios of PBMCs: MCF-7 cells (E:T) for 4 hr. The amount of cell lysis was determined by the lactate dehydrogenase (LDH) release assay and compared to non-functionalized PBMCs and PBMCs treated with an irrelevant anti-CD22-Lipid-CSANs.26 At the end of four hours a two-fold increase in cell lysis was observed for E:T ratios ranging from 1:1 to 50:1 compared to untreated or irrelevant controls, with 90% cell lysis achieved at an E:T ratio of 50:1. (FIG. 4A, S7) These results compare favorably with the observed induced cell lysis of EpCAM positive tumor cells in vitro for anti-CD3×anti-EpCAM bispecific antibodies over the same time period. 27 To determine the dependence of the observed T-cell induced cell lysis on the loading concentration of the anti-EpCAM-Lipid-CSANs, the amount of cell lysis was determined for variable concentrations of anti-EpCAM-Lipid-CSANs at a fixed E:T ratio of 10:1. As can be seen from FIG. 4B, for 1.5×105 cells, a concentration as low as 50 nM of the anti-EpCAM-Lipid-CSANs was able to generate maximum cell lysis.

Figure 4C:
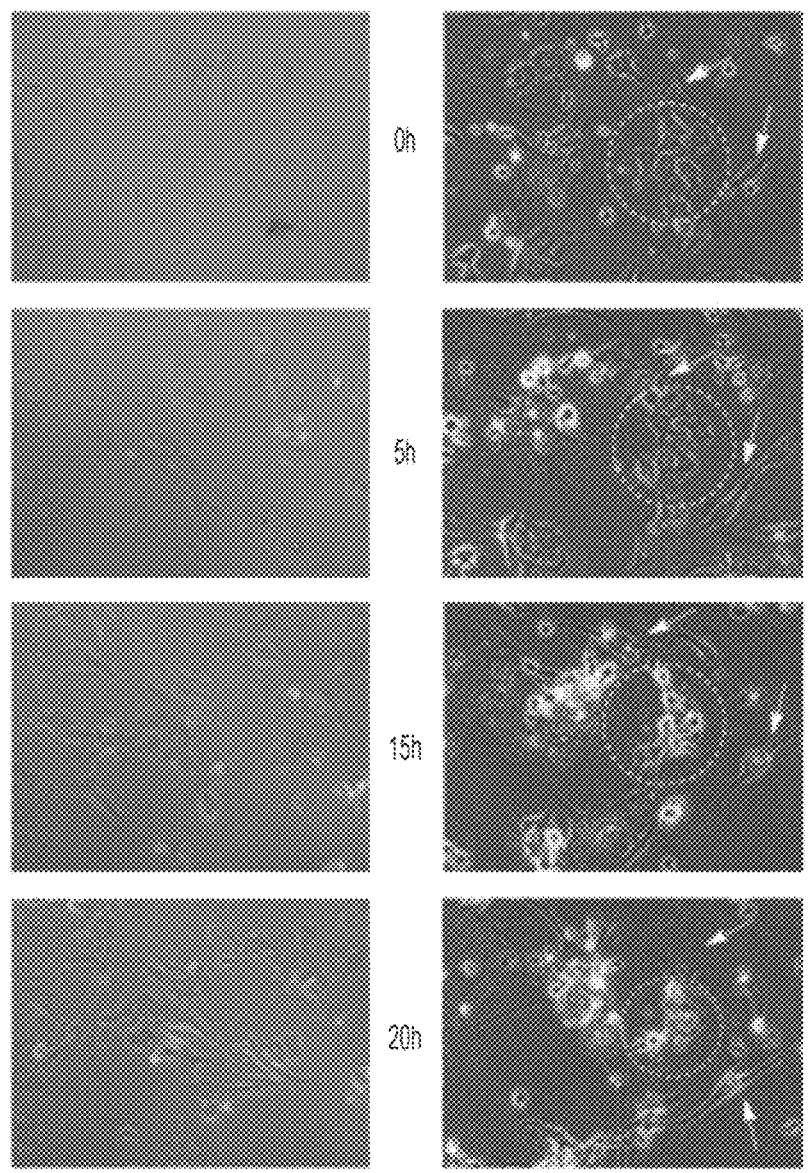

To observe the selectivity of anti-EpCAM-Lipid-CSANs modified PBMCs, time-lapse microscopy was performed. Target MCF-7 cells were co-cultured with EpCAM negative U87 glioblastoma cells at a one to one ratio. Upon the addition of anti-EpCAM CSARs treated PBMCs (at a E:T ratio of 1:2), specific and selective cell lysis of the MCF-7 cells was observed over the course of twenty hours specific, while the U87 cells remained healthy and maintained a normal morphology. (FIG. 4 C) While the U87 cells continued to divide and move along the plane of the plate, the anti-EpCAM-Lipid-CSANs modified PBMCs were effectively redirected towards the MCF-7 cells resulting in the initiation of apoptosis between 5 and 15 hrs. Cell blebbing, plasma membrane disruption and in some cases cell rupture were observed. (FIG. 4C) In contrast, when MCF-7 and U87 cells were incubated with untreated activated PBMCs, no apparent cell lysis was observed. Consistent with these observations, cytotoxicity studies demonstrated that while the cytotoxicity modified PBMCs to MCF-7 cells was significantly enhanced, no enhanced cytotoxicity to U87 cells was observed. (FIG. S6) Thus, the anti-EpCAM-Lipid- CSANs are able to not only redirect PBMCs towards the intended target cells, but also to cause selective target antigen directed cell lysis.

These results demonstrate that CSANs can be used as a molecular scaffold to stably and non-genetically engineer cell surfaces. In addition, temporal pharmacological control over the designed cell-cell interactions can be exerted by treatment with the non-toxic FDA approved antibiotic, trimethoprim. The application of this approach to the design of anti-EpCAM-Lipid-CSANs demonstrates that this approach has the potential to be a complementary methodology for quickly exploring the feasibility of a ligand for adoptive T-cell therapy, as well as a general approach for the development of a synthetic biological tool kit for the reversible modification of cell surfaces and the engineering of cell-cell interactions.

All documents cited herein are incorporated by reference. While certain embodiments of invention are described, and many details have been set forth for purposes of illustration, certain of the details can be varied without departing from the basic principles of the invention.

The use of the terms "a" and "an" and "the" and similar terms in the context of describing embodiments of invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. In addition to the order detailed herein, the methods described herein can be performed in any suitable order unless otherwise indicated herein or otherwise clearly contradicted by context. The use of any and all examples, or exemplary language (e.g., "such as") provided herein, is intended merely to better illuminate embodiments of invention and does not necessarily impose a limitation on the scope of the invention unless otherwise specifically recited in the claims. No language in the specification should be construed as indicating that any non-claimed element is essential to the practice of the invention.

What is claimed is:

1. A compound of formula I:

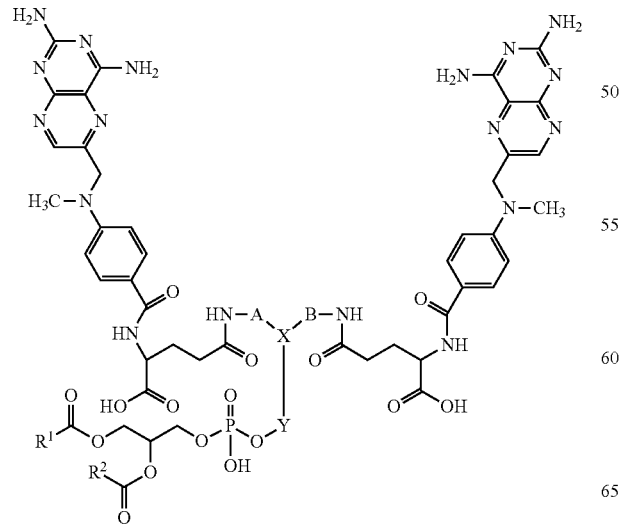

wherein:

A is a divalent, branched or unbranched, saturated or unsaturated, hydrocarbon chain, having from 2 to 25 carbon atoms, wherein one or more of the carbon atoms is optionally replaced by (—O—), and wherein the chain is optionally substituted on carbon with one or more substituents selected from $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo (=O), carboxy, aryl, aryloxy, heteroaryl, and heteroaryloxy;

B is a divalent, branched or unbranched, saturated or unsaturated, hydrocarbon chain, having from 2 to 25 carbon atoms, wherein one or more of the carbon atoms is optionally replaced by (—O—), and wherein the chain is optionally substituted on carbon with one or more substituents selected from $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo (=O), carboxy, aryl, aryloxy, heteroaryl, and heteroaryloxy;

X is N or

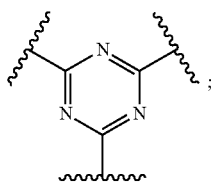 [SMILES: *c1nc(*)nc(*)n1]

Y is a divalent, branched or unbranched, saturated or unsaturated, hydrocarbon chain, having from 20 to 250 carbon atoms, wherein one or more of the chain carbon atoms is optionally replaced by O, S, $NR^a$, (C=O) or a 5 or 6-membered heterocycle, wherein each $R^a$ is independently H or $(C_1-C_6)$alkyl, and wherein the chain is optionally substituted on carbon with one or more substituents selected from $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo (=O), carboxy, aryl, aryloxy, heteroaryl and heteroaryloxy;

$R^1$ is a branched or unbranched, saturated or unsaturated, hydrocarbon chain, having from 3 to 30 carbon atoms; and $R^2$ is a branched or unbranched, saturated or unsaturated, hydrocarbon chain, having from 3 to 30 carbon atoms;

or a salt thereof.

2. The compound of claim 1 which is a compound of formula Ia:

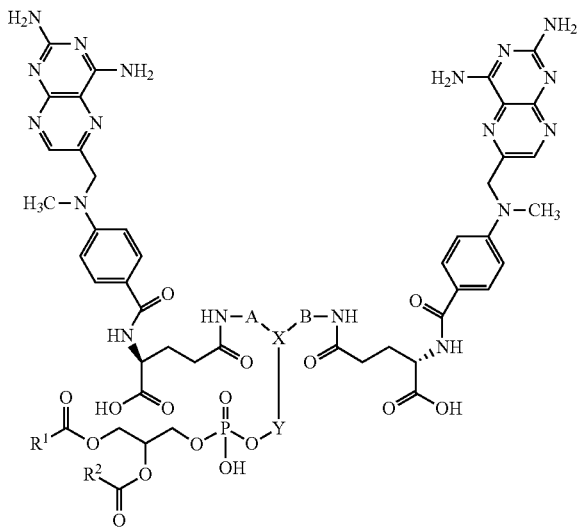

Ia wherein:
- A is a divalent, branched or unbranched, saturated or unsaturated, hydrocarbon chain, having from 2 to 25 carbon atoms, wherein one or more of the carbon atoms is optionally replaced by (—O—), and wherein the chain is optionally substituted on carbon with one or more substituents selected from $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo (=O), carboxy, aryl, aryloxy, heteroaryl, and heteroaryloxy;
- B is a divalent, branched or unbranched, saturated or unsaturated, hydrocarbon chain, having from 2 to 25 carbon atoms, wherein one or more of the carbon atoms is optionally replaced by (—O—), and wherein the chain is optionally substituted on carbon with one or more substituents selected from $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo (=O), carboxy, aryl, aryloxy, heteroaryl, and heteroaryloxy;
- X is N or

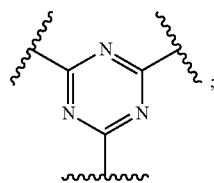 [SMILES: *c1nc(*)nc(*)n1]

- Y is a divalent, branched or unbranched, saturated or unsaturated, hydrocarbon chain, having from 20 to 250 carbon atoms, wherein one or more of the chain carbon atoms is optionally replaced by O, S, $NR^a$, (C=O) or a 5 or 6-membered heterocycle, wherein each $R^a$ is independently H or $(C_1-C_6)$alkyl, and wherein the chain is optionally substituted on carbon with one or more substituents selected from $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo (=O), carboxy, aryl, aryloxy, heteroaryl and heteroaryloxy;
- $R^1$ is a branched or unbranched, saturated or unsaturated, hydrocarbon chain, having from 3 to 30 carbon atoms; and
- $R^2$ is a branched or unbranched, saturated or unsaturated, hydrocarbon chain, having from 3 to 30 carbon atoms; or a salt thereof.

3. The compound of claim 1, wherein A is a divalent, branched or unbranched, saturated or unsaturated, hydrocarbon chain, having from 3 to 10 carbon atoms, wherein one or more carbon atoms is optionally replaced with an oxygen (—O—) atom in the chain, wherein the chain is optionally substituted on carbon with one or more substituents selected from $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo (=O), carboxy, aryl, aryloxy, heteroaryl, and heteroaryloxy.

4. The compound of claim 1, wherein A is a divalent, branched or unbranched, saturated or unsaturated, hydrocarbon chain, having from 3 to 10 carbon atoms.

5. The compound of claim 1, wherein B is a divalent, branched or unbranched, saturated or unsaturated, hydrocarbon chain, having from 3 to 10 carbon atoms, wherein one or more carbon atoms is optionally replaced with an oxygen (—O—) atom in the chain, wherein the chain is optionally substituted on carbon with one or more substituents selected from $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo(=O), carboxy, aryl, aryloxy, heteroaryl, and heteroaryloxy.

6. The compound of claim 1, wherein B is a divalent, branched or unbranched, saturated or unsaturated, hydrocarbon chain, having from 3 to 10 carbon atoms.

7. The compound of claim 1, wherein X is N.

8. The compound of claim 1, wherein $R^1$ is a branched or unbranched, saturated or unsaturated, hydrocarbon chain, having from 10 to 25 carbon atoms.

9. The compound of claim 1, wherein $R^2$ is a branched or unbranched, saturated or unsaturated, hydrocarbon chain, having from 10 to 25 carbon atoms.

10. The compound of claim 1, wherein Y has a molecular weight of from about 200 daltons to about 10,000 daltons.

11. The compound of claim 1, wherein Y is divalent, branched or unbranched, saturated or unsaturated, hydrocarbon chain, having from 50 to 250 carbon atoms, wherein one or more of the chain carbon atoms is optionally replaced by O, S, $NR^a$, (C=O) or a 5 or 6-membered heterocycle and wherein each $R^a$ is independently H or $(C_1-C_6)$alkyl.

12. The compound of claim 1, wherein Y is divalent, branched or unbranched, saturated or unsaturated, hydrocarbon chain, having from 100 to 250 carbon atoms, wherein one or more of the chain carbon atoms is optionally replaced by O, S, $NR^a$, (C=O) or a 5 or 6-membered heterocycle and wherein each $R^a$ is independently H or $(C_1-C_6)$alkyl.

13. The compound of claim 1, wherein Y is divalent, branched or unbranched, saturated or unsaturated, hydrocarbon chain, having from 100 to 200 carbon atoms, wherein one or more of the chain carbon atoms is optionally replaced by O, S, $NR^a$, (C=O) or a 5 or 6-membered heterocycle and wherein each $R^a$ is independently H or $(C_1-C_6)$alkyl.

14. The compound of claim 12, wherein one or more of the chain carbon atoms is optionally replaced by O, S, $NR^a$ or (C=O) wherein each $R^a$ is independently H or $(C_1-C_6)$ alkyl and wherein 1, 2 or 3 of the chain carbon atoms is optionally replaced by a 5 or 6-membered heterocycle.

15. The compound of claim 1 which is:

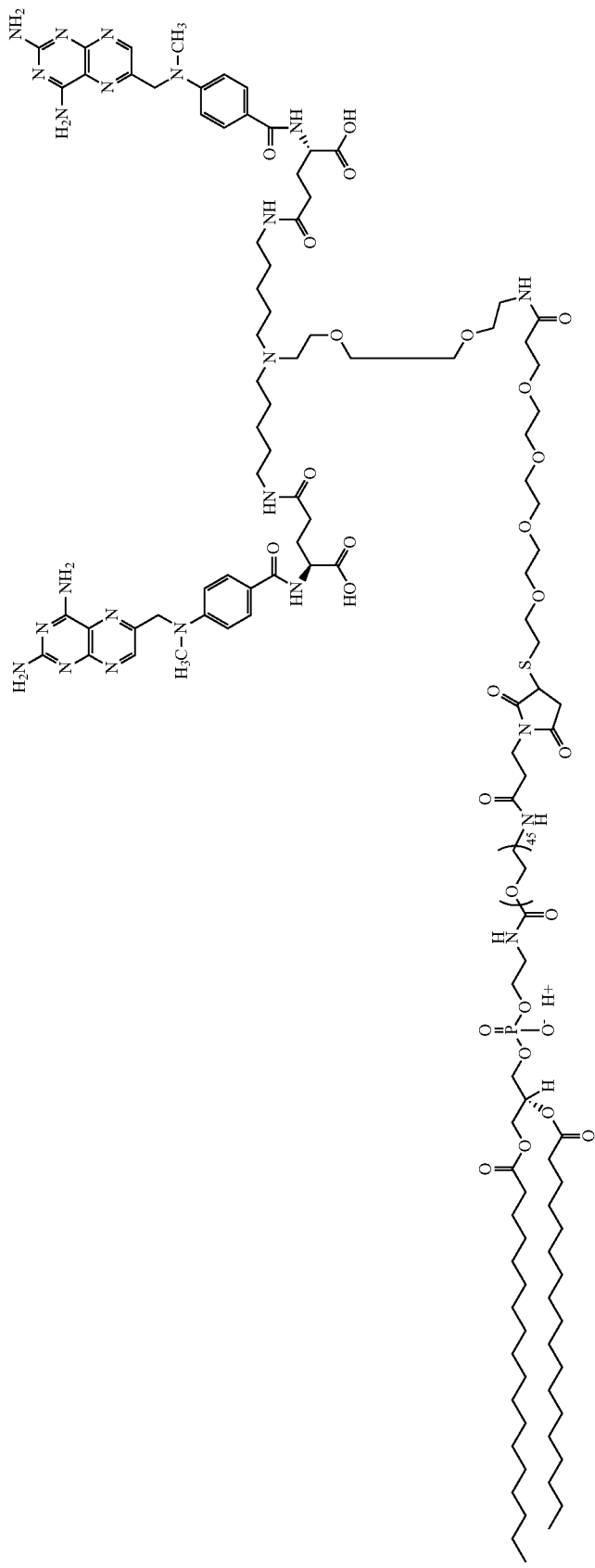

16. A conjugate comprising a compound of formula I or a salt thereof as described in claim 1, wherein the conjugate further comprises a first dihydrofolate reductase (DHFR) molecule linked to second DHFR molecule via a linker.

17. A composition comprising a compound of formula I or a pharmaceutically acceptable salt thereof or a conjugate of formula I or a pharmaceutically acceptable salt thereof as described in claim 1 and a pharmaceutically acceptable carrier.

18. A method for treating cancer in a patient in need of such treatment, comprising administering to the patient a therapeutically effective amount of a compound of formula I or a pharmaceutically acceptable salt thereof as described in claim 1.

19. A method to modify the surface of a cell comprising contacting the cell in vitro or in vivo with a compound of formula I or a pharmaceutically acceptable salt thereof as described in claim 1.

* * * * *

UNITED STATES PATENT AND TRADEMARK OFFICE
CERTIFICATE OF CORRECTION

PATENT NO. : 9,499,800 B2  
APPLICATION NO. : 14/581538  
DATED : November 22, 2016  
INVENTOR(S) : Carston R. Wagner Page 1 of 1

It is certified that error appears in the above-identified patent and that said Letters Patent is hereby corrected as shown below:

In the Specification

Column 1, Lines 14-16, Statement of Government Support, please delete "This invention was made with government support under CA125360 and CA120116 awarded by the National Cancer Institute." and insert -- This invention was made with government support under CA120116 and CA125360 awarded by the National Institutes of Health. The government has certain rights in the invention. -- therefor.

Signed and Sealed this  
Seventeenth Day of September, 2019

Andrei Iancu  
*Director of the United States Patent and Trademark Office*